United States Patent
Brun et al.

(10) Patent No.: US 7,951,207 B2
(45) Date of Patent: May 31, 2011

(54) COMPOSITION FOR DYEING KERATIN FIBERS, COMPRISING AT LEAST ONE POLYALKENE-BASED SUPRAMOLECULAR POLYMER, AT LEAST ONE PIGMENT AND AT LEAST ONE VOLATILE SOLVENT

(75) Inventors: Gaëlle Brun, Paris (FR); Sandrine Chodorowski-Kimmes, Senlis (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/624,718

(22) Filed: Nov. 24, 2009

(65) Prior Publication Data

US 2010/0154134 A1 Jun. 24, 2010

Related U.S. Application Data

(60) Provisional application No. 61/118,028, filed on Nov. 26, 2008.

(30) Foreign Application Priority Data

Nov. 24, 2008 (FR) ..................................... 08 57936

(51) Int. Cl.
*A61Q 5/10* (2006.01)
(52) U.S. Cl. ............. 8/405; 8/435; 8/552; 8/567; 8/581; 8/637.1
(58) Field of Classification Search ............... 8/405, 435, 8/552, 567, 581, 637.1
See application file for complete search history.

(56) References Cited

U.S. PATENT DOCUMENTS

| | | | |
|---|---|---|---|
| 6,572,729 | B1 | 6/2003 | Auvray et al. |
| 2001/0053377 | A1 | 12/2001 | Mondet et al. |
| 2003/0017182 | A1 | 1/2003 | Tournilhac |
| 2004/0161394 | A1* | 8/2004 | Mougin et al. ............. 424/70.11 |
| 2007/0189991 | A1 | 8/2007 | Mougin et al. |
| 2008/0127429 | A1 | 6/2008 | Brun et al. |
| 2009/0130028 | A1 | 5/2009 | Rollat-Corvol et al. |

FOREIGN PATENT DOCUMENTS

| | | |
|---|---|---|
| EP | 1 155 687 A1 | 11/2001 |
| EP | 1 392 222 B1 | 3/2004 |
| EP | 1 435 900 B1 | 7/2004 |
| EP | 1 797 868 A1 | 6/2007 |
| EP | 1 944 064 A2 | 7/2008 |
| FR | 2 741 530 A1 | 5/1997 |
| FR | 2 782 723 A1 | 3/2000 |
| FR | 2 816 503 A1 | 5/2002 |
| FR | 2 825 628 A1 | 12/2002 |
| FR | 2 907 674 A1 | 5/2008 |
| FR | 2 907 678 A1 | 5/2008 |
| WO | WO 02/098377 A1 | 12/2002 |
| WO | WO 03/032929 A2 | 4/2003 |
| WO | WO 2005/042641 A1 | 5/2005 |
| WO | WO 2007/039832 A2 | 4/2007 |

OTHER PUBLICATIONS

STIC Search Report dated Jul. 13, 2010.*
Brigitte J.B. Folmer et al., "Supramolecular Polymer Materials: Chain Extension of Telechelic Polymers Using a Reactive Hydrogen-Bonding Synthon," Advanced Materials, vol. 12, No. 12, pp. 874-878, 2000.
Database Biosis [Online], Biosciences Information Service, Ikkala Olli et al, "Functional Materials Based on Self-assembly of Polymeric Supramolecules," Mar. 29, 2002, XP002538770.
Co-pending Application filed Nov. 24, 2009.
French Search Report for FR 0857936, dated Jul. 27, 2009.
French Search Report for FR 0857939, dated Oct. 29, 2009.
English language abstract of FR 2 907 674 A1, May 2, 2008.

\* cited by examiner

*Primary Examiner* — Eisa B Elhilo
(74) *Attorney, Agent, or Firm* — Finnegan, Henderson, Farabow, Garrett & Dunner, LLP

(57) ABSTRACT

The present disclosure relates to a composition for dyeing keratin fibers, comprising at least one polyalkene-based supramolecular polymer, at least one pigment and at least one volatile solvent, wherein the weight ratio of the at least one supramolecular polymer to the at least one pigment has a value greater than 0.25, and also a process for dyeing keratin fibers using this composition. The present disclosure may make it possible to obtain, on the keratin fibers, colored coatings for keeping the hairs individualized while at the same time preserving the physical qualities of the fiber.

15 Claims, No Drawings

COMPOSITION FOR DYEING KERATIN FIBERS, COMPRISING AT LEAST ONE POLYALKENE-BASED SUPRAMOLECULAR POLYMER, AT LEAST ONE PIGMENT AND AT LEAST ONE VOLATILE SOLVENT

This application claims benefit of U.S. Provisional Application No. 61/118,028, filed Nov. 26, 2008, the contents of which are incorporated herein by reference. This application also claims benefit of priority under 35 U.S.C. §119 to French Patent Application No. FR 0857936, filed Nov. 24, 2008, the contents of which are also incorporated herein by reference.

The present disclosure relates to a composition for dyeing keratin fibers, for example human keratin fibers such as the hair or the eyelashes, comprising at least one polyalkene-based supramolecular polymer, at least one pigment and at least one volatile solvent, wherein the weight ratio of the at least one polyalkene-based supramolecular polymer to the at least one pigment has a value greater than 0.25.

In the keratin-fiber dyeing field, it is already known practice to dye keratin fibers by various techniques using direct dyes for nonpermanent colorations or dye precursors for permanent colorations.

Nonpermanent dyeing or direct dyeing consists in dyeing the keratin fibers with dye compositions containing direct dyes. These dyes may be colored or coloring molecules that have an affinity for keratin fibers. They may be applied to the keratin fibers for a period of time necessary to obtain the desired coloration, and then rinsed off.

The conventional dyes that may be used are, for example, nitrobenzene, anthraquinone, nitropyridine, azo, xanthene, acridine, azine or triarylmethane dyes, or natural dyes.

Some of these dyes can be used under lightening conditions, thereby making it possible to obtain visible colorations on dark hair.

It is also known practice to dye keratin fibers permanently by oxidation dyeing. This dyeing technique consists in applying, to the keratin fibers, a composition containing dye precursors such as oxidation bases and couplers. Under the action of an oxidizing agent, these precursors will form at least one colored substance in the hair.

The variety of molecules used as oxidation bases and couplers allows a wide range of colors to be obtained, and the colorations resulting therefrom are generally permanent, strong and resistant to external agents, for example to light, bad weather, washing, perspiration and rubbing.

In order to be visible on dark hair, these two dyeing techniques may require prior or simultaneous bleaching of the keratin fibers. This bleaching step, carried out with an oxidizing agent such as hydrogen peroxide or persalts, may result in appreciable degradation of the keratin fibers, which may impair their cosmetic properties. The hair then may have a tendency to become coarse, more difficult to disentangle and/or more brittle.

Another dyeing method consists in using pigments. Specifically, the use of pigment at the surface of keratin fibers generally makes it possible to obtain visible colorations on dark hair, since the surface pigment masks the natural color of the fiber.

The colorations obtained via this dyeing method may have the drawback of being removed as soon as the first shampooing operation.

Thus, the present disclosure relates to a composition for dyeing keratin fibers, for example human keratin fibers such as the hair or the eyelashes, which may make it possible to obtain colored coatings that are fast with respect to shampoo and/or to the various attacks to which the hair may be subjected, without degrading the keratin fibers and/or while keeping the hairs perfectly individualized.

Accordingly, disclosed herein is a composition for dyeing keratin fibers, for example human keratin fibers such as the hair or the eyelashes, comprising at least one polyalkene-based supramolecular polymer, at least one pigment and at least one volatile solvent, wherein the weight ratio of the at least one supramolecular polymer to the at least one pigment is greater than 0.25, for example ranging from 0.3 to 20, or for example from 0.4 to 10, or for example from 0.5 to 5.

The compositions in accordance with the present disclosure may make it possible to obtain, on keratin fibers, colored coatings that make it possible to obtain a shampoo-fast visible coloration on all hair types, for example on dark hair, while at the same time preserving the physical qualities of the keratin fiber. Such a coating may be, for example, resistant to the external attacks to which the hair may be subjected, such as blow-drying and perspiration. It may make it possible, for example, to obtain a smooth, uniform deposit. Moreover, it has been observed, surprisingly, that the hairs may remain individualized, and may be styled without problems.

As used herein, the term "individualized hairs" is intended to mean hairs which, after application of the composition and drying, are not stuck together (or are all separate from one another) and therefore do not form clumps of hair, since the coating is formed around virtually every hair.

Another aspect of the present disclosure is also a process for dyeing keratin fibers, for example human keratin fibers such as the hair or the eyelashes, using this composition.

One aspect of the present disclosure is also the use of this composition for obtaining a colored coating on the hair.

In the subsequent text, unless otherwise indicated, the limits of the ranges indicated are included in the ranges.

Polyalkene-based Supramolecular Polymers

As used herein, the term "polyalkene-based supramolecular polymer" is intended to mean a polymer comprising, in its structure, at least one polyalkene part and at least one part comprising at least one group capable of forming at least three H-bonds, such as at least four H-bonds.

In at least one embodiment, the at least one polyalkene part is chosen from poly(ethylene-butylene)s, polybutadienes and polyisoprenes.

In at least one embodiment, the polyalkene-based supramolecular polymer(s) of the disclosure may be obtained by condensing at least one polyalkene polymer functionalized with at least one reactive group (a), with at least one graft functionalized with at least one reactive group (b), wherein the at least one reactive group (b) is capable of reacting with the at least one reactive group (a), and wherein the at least one graft comprises at least one group capable of forming at least three H-bonds, such as at least four H-bonds.

For example, the at least one functionalized polyalkene polymer can be chosen from those of formula:

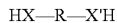

wherein XH and X'H are reactive groups, with X and X', which are identical or different, chosen from O, S, NH or $NR_a$, $R_a$ representing a $C_1$-$C_6$ alkyl group. In at least one embodiment, X and/or X' denote O;

R represents a homopolymer or a copolymer derived from at least one monounsaturated or polyunsaturated $C_2$-$C_{10}$ alkene, such as $C_2$-$C_4$, alkenes; in one embodiment, R is chosen from poly(ethylene-butylene)s, polybutadienes and poly-isoprenes.

Poly(ethylene-butylene)s are copolymers of 1-butene and of ethylene, which can be represented schematically by the series of the following units:

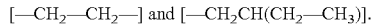

The polybutadienes may be 1,4-polybutadienes or 1,2-polybutadienes, which can be respectively represented schematically by the series of units below:

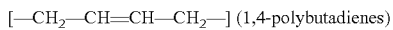

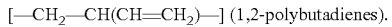

For example, the polybutadienes can be 1,2-polybutadienes.

For example, the functionalization may be carried out at the end of the chains. The term "telechelic polymers" is then used. The functionalizing groups can be attached to the polyalkene polymer via linkers, such as linear or branched $C_1$-$C_4$ alkylene groups.

The at least one poly(alkene) part may be hydrogenated so as to avoid the risks of crosslinking.

The at least one poly(alkene) part may comprise, in its structure, other units derived from other monomers. As comonomers, exemplary mention may be made of styrene.

For example, the polymeric backbone(s) may be chosen from hydroxyl-terminated polydienes, which in at least one embodiment are hydrogenated, and hydroxyl-terminated polyolefins.

These hydroxyl-terminated polydienes are defined, for example, in French Patent No. FR 2 782 723. In at least one embodiment, they are chosen from the group consisting of homopolymers and copolymers of polybutadiene, of polyisoprene and of poly(1,3-pentadiene). They are oligomers with a number-average molecular mass of less than 7,000, and in at least one embodiment ranging from 1,000 to 5,000. For example, they can have a terminal hydroxyl functionality ranging from 1.8 to 3, such as in the region of 2.

Exemplary mention may be made of the hydroxylated polybutadienes sold by the company Elf Atochem under the trademarks POLY BD R-45HT and POLY BD R-20 LM, which may be used hydrogenated. Exemplary mention may also be made of di-OH hydrogenated (1,2-polybutadiene)s, such as the GI3000 of Mn=2600-3200 and the GI2000 of Mn=1800-2200 sold by the company Nisso.

Use may also be made of α,ω-hydroxyl-terminated polyolefins, homopolymers or copolymers, such as:
α,ω-hydroxyl-terminated polyisobutylene oligomers;
the copolymers sold by the company Mitsubishi under the trademark POLYTAIL with, for example, those corresponding to the formula:

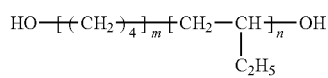

The supramolecular polymers of the present disclosure have, in their structure, at least one graft which carries at least one group capable of forming at least three H-bonds, such as at least four H-bonds.

These groups capable of forming at least three H-bonds may comprise, for example, at least three functional groups, such as at least four, chosen from the following formulae:

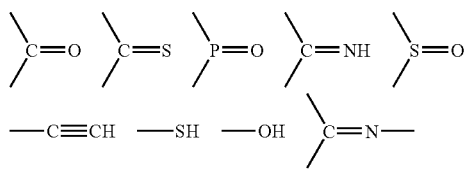

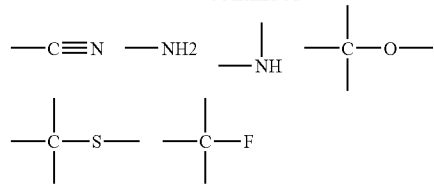

These functional groups may be classified in two categories:
H-bond-donor functional groups such as the groups:

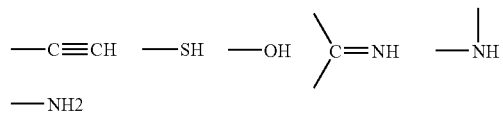

and H-bond-acceptor functional groups such as the groups:

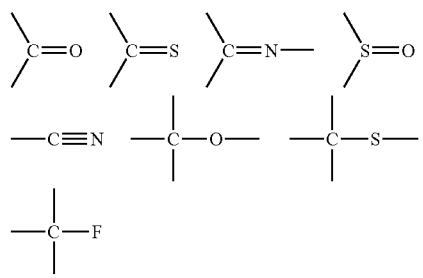

The groups capable of forming at least three H-bonds form a basic structural element comprising at least three functional groups, such as at least four functional groups, capable of establishing H-bonds. The basic structural elements capable of establishing three or four H-bonds may be represented schematically in the following way:

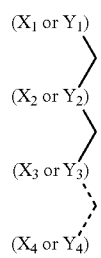

wherein $X_i$ (i being a natural integer) is an H-bond-acceptor functional group and $Y_i$ is an H-bond-donor functional group.

Thus, each structural element should be able to establish H-bonds with at least one partner structural element, which may be identical (i.e. self-complementary) or different, such that each pairing of two partner structural elements takes place by formation of at least three H-bonds, such as at least four H-bonds.

A proton acceptor X will pair with a proton donor Y.
Several possibilities are offered, for example pairing of:
XXXX with YYYY;
XXXY with YYYX;

XXYX with YYXY;
XYYX with YXXY;
XXYY with YYXX, self-complementary or not;
XYXY with YXYX, self-complementary or not.

In at least one embodiment, the groups can establish four H-bonds with an identical (or self-complementary) partner group, among which bonds are two donor bonds (for example, NH) and two acceptor bonds (for example, CO and —C=N—).

In another embodiment, the groups capable of forming at least three H-bonds comprise rings with 5 or 6 atoms (unsaturated heterocycles or aromatic rings), for example those constituted of C and/or N atoms, and, for example, comprising conjugated double bonds in order to stabilize and direct the H interactions.

For example, the groups capable of forming at least three H-bonds may be involved in rings with 6 atoms comprising C and/or N atoms and comprising conjugated double bonds in order to stabilize and direct the H interactions.

According to at least one embodiment, the groups capable of forming three or four H-bonds are chosen from the following families, it being understood that all the tautomeric forms are included:

(i) aminopyrimidones of formula:

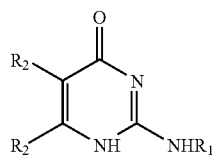

(ii) ureidopyrimidones of formula:

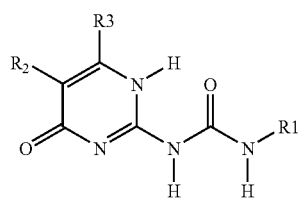

(iii) acylaminopyridines, such as:
monoacylaminopyridines of formula:

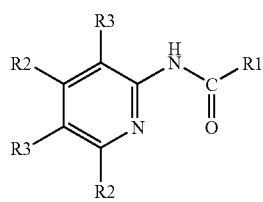

di(acylamino)pyridines, for example 2,6-di(acylamino) pyridines of formula:

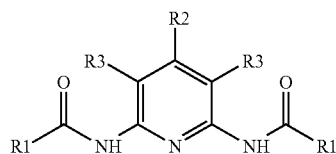

(iv) aminopyrimidines, such as:
aminopyrimidines of formulae:

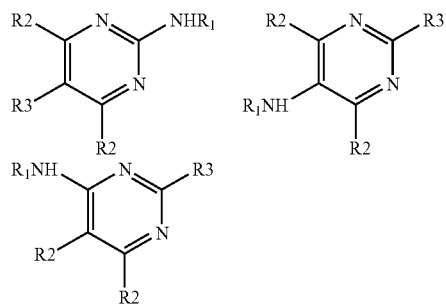

diaminopyrimidines of formulae:

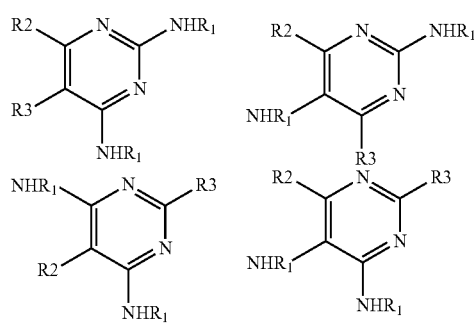

or triaminopyrimidines;

(v) ureidotriazines, such as mono-, di- and triureidotriazines, for example the ureidoaminotriazines of formula:

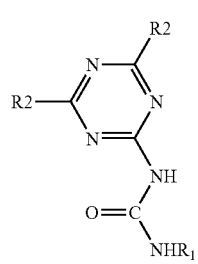

(vi) (acylamino)triazines, such as mono-, di- and tri(acylamino)triazines, optionally amino (mono-, di- or triamino), for example:
di(acylamino)triazines of formula:

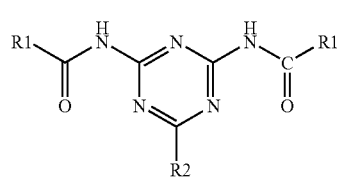

(acylamino)aminotriazines (mono- or di(acylamino), and mono- or diamino), such as compounds of formula:

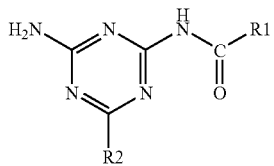

(acylamino)triazines of formula:

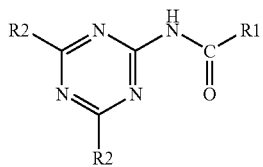

or tri(acylamino)triazines;
(vii) aminotriazines, such as:
monoaminotriazines;
2,6-diamino-s-triazines of formula:

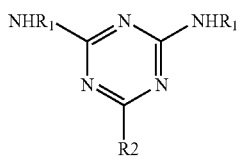

triamino-s-triazines of formula:

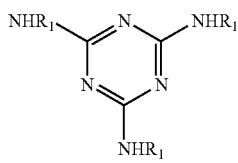

(viii) acylaminotriazoles of formula:

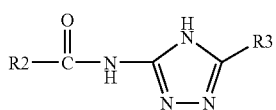

(ix) urazoylbenzoic acids of formula:

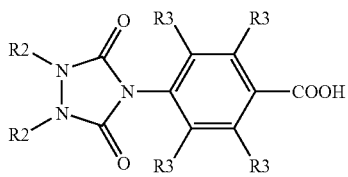

(x) phthalhydrazides of formula:

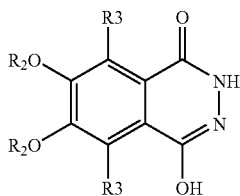

(xi) uracils of formula:

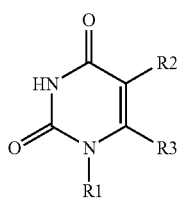

(xii) thymines of formula:

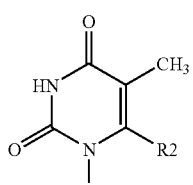

(xiii) succinimides of formula:

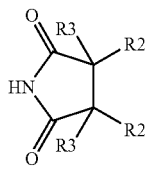

(xiv) glutarimides of formula:

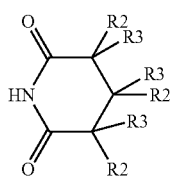

(xv) compounds of the cyanuric acid family of formula:

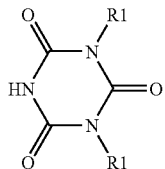

(xvi) maleimides of formula:

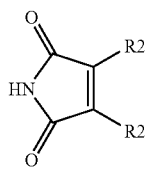

(xvii) compounds of the barbituric acid family, of formula:

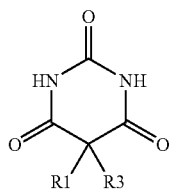

(xviii) compounds of the following formulae:

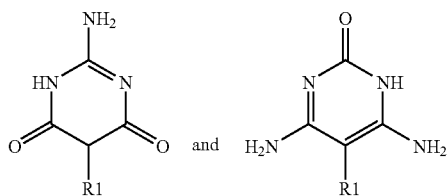

(xix) compounds of the trimellitic acid family, of formula:

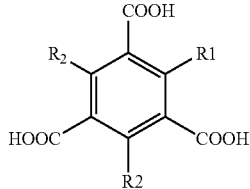

(xx) ureidopyridines, such as mono- or diureidopyridines, for example those of formulae:

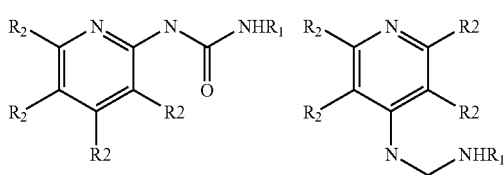

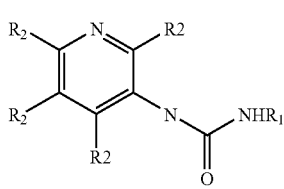

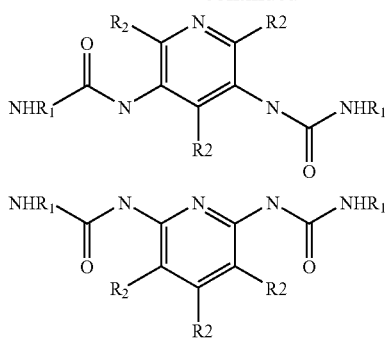

(xxi) carbamoylpyridines of formulae:

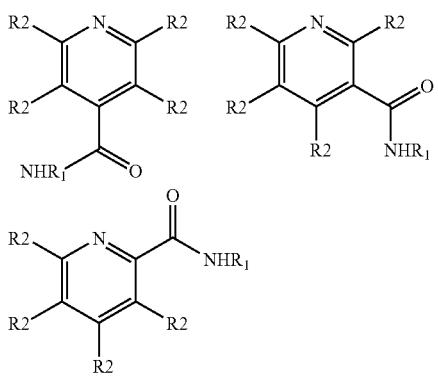

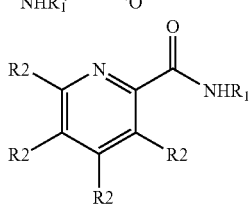

(xxii) adenines of formula:

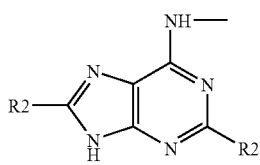

(xxiii) guanines of formula:

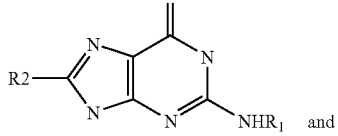 and (xxiv) cytidines of formula:

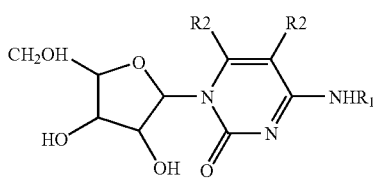

In all the above formulae, the meaning of the radicals are the following:
(a) the $R_1$ radicals, which may be identical or different, represent a single bond, a hydrogen atom, a halogen atom and/or a saturated or unsaturated, optionally aromatic, linear, branched or cyclic monovalent $C_1$-$C_{6000}$ carbon-based group (such as alkyl) optionally comprising at least one heteroatom such as O, S, N, P, Cl, Br or F; or a combination of these meanings.

In one embodiment, the $R_1$ radicals are chosen from $C_4$-$C_{12}$ cycloalkyl groups, linear or branched $C_1$-$C_{30}$ alkyl groups and $C_4$-$C_{12}$ aryl groups, optionally substituted with an amino, ester and/or hydroxyl function.

In another embodiment, $R_1$ radicals are chosen from $C_4H_9$; phenyl; 1,4-nitrophenyl; 1,2-ethylene; 1,6-hexylene; 1,4-butylene; 1,6-(2,4,4-trimethylhexylene); 1,4-(4-methylpentylene); 1,5-(5-methylhexylene); 1,6-(6-methylheptylene); 1,5-(2,2,5-tri-methylhexylene); 1,7-(3,7-dimethyloctylene); -isophorone-; 4,4'-methylenebiscyclohexylene; tolylene; 2-methyl-1,3-phenylene; 4-methyl-1,3-phenylene; and 4,4-biphenylenemethylene;

and in a further embodiment, chosen from -isophorone-; —$(CH_2)_2$—; —$(CH_2)_6$—; —$CH_2CH(CH_3)$—$CH_2$—C($CH_3)_2$—$CH_2$—$CH_2$; 4,4'-methylenebiscyclohexylene; and 2-methyl-1,3-phenylene.

In at least one embodiment, $R_1$ is a single bond.

(b) the $R_2$ radicals, which may be identical or different are chosen from single bonds; hydrogen atoms; halogen atoms (such as —Br, —Cl, or —F); —OH or —$N(R)_2$ radicals (with R being H or a linear or branched $C_1$-$C_{12}$, such as a $C_1$-$C_4$ alkyl radical, for example a methyl or ethyl radical); saturated or unsaturated, optionally aromatic, linear, branched or cyclic monovalent $C_1$-$C_{6000}$ hydrocarbon-based groups that may optionally comprise at least one heteroatom such as O, S, N, P or F; or a combination of these meanings.

For example, the $R_2$ radicals can be chosen from H, CN, $NH_2$, and the following groups:
$C_1$-$C_{30}$ alkyl groups;
$C_4$-$C_{12}$ cycloalkyl groups;
$C_4$-$C_{12}$ aryl groups;
$(C_4$-$C_{12})$aryl$(C_1$-$C_{30})$alkyl groups;
$C_1$-$C_4$ alkoxy groups;
arylalkoxy groups, such as $(C_1$-$C_4)$arylalkoxy groups;
$C_4$-$C_{12}$ heterocycles;
thioalkoxy groups;
sulphoxy groups;
or mixtures thereof, these groups being optionally substituted with an amino, ester and/or hydroxyl function.

In at least one embodiment, $R_2$ is chosen from H, $CH_3$, $C_{13}H_{27}$, $C_7H_{15}$ and phenyl.

(c) the $R_3$ radicals, which may be identical or different, are chosen from hydrogen atoms; saturated or unsaturated, optionally aromatic, linear, branched or cyclic monovalent $C_1$-$C_{6000}$ hydrocarbon-based groups that may optionally comprise at least one heteroatom such as O, S, N, P or F; and combinations thereof.

For example, the $R_3$ radical may be chosen from $C_4$-$C_{12}$ cycloalkyl groups, linear or branched $C_1$-$C_{30}$ alkyl groups, and $C_4$-$C_{12}$ aryl groups, optionally substituted with an amino, ester and/or hydroxyl function. In at least one embodiment, the $R_3$ radical represents a methyl radical.

In all of these formulae, it is understood that at least one, for example one or two, of the $R_1$ and/or $R_2$ groups is a single bond constituting the point of attachment of the at least one group capable of forming at least three H-bonds on the residue of the at least one graft.

For example, the point of attachment can be carried by $R_1$ and/or $R_2$, and in at least one embodiment it is carried by $R_1$.

For example, the at least one group capable of forming at least three H-bonds can be chosen from:
(a) groups capable of forming at least three H-bonds which are complementary and identical, i.e. self-complementary, such as:
aminopyrimidones, or ureidopyrimidones,
compounds of the trimellitic acid family or of the urazoylbenzoic acid family,
acylaminopyridines, ureidopyridines, or carbamoylpyridines,
acylaminotriazines, ureidotriazines, such as ureidoaminotriazines, or diaminotriazines,
acylaminotriazoles,
phthalhydrazides,
compounds of formulae:

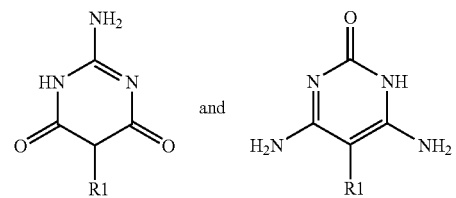

wherein $R_1$ is chosen from hydrogen atoms and saturated or unsaturated, optionally aromatic, linear, branched or cyclic monovalent $C_1$-$C_{6000}$ hydrocarbon-based groups that may optionally comprise at least one heteroatom such as O, S, N, P or F; and (b) groups capable of forming at least three H-bonds which are complementary but different, such as:
adenine complementary to guanine,
cytidine complementary to thymine,
triamino-s-triazine complementary to uracil or to succinimide or to glutarimide or to cyanuric acid or to thymine or to maleimide or to (di)aminopyrimidine or to barbituric acid,
(acylamino)amino-s-triazine complementary to uracil or to succinimide or to glutarimide or to cyanuric acid or to thymine or to maleimide or to (di)aminopyrimidine or to barbituric acid.

For example, the at least one group capable of forming at least three H-bonds can be chosen from groups capable of establishing at least three H-bonds with themselves (self-complementary), such as at least four H-bonds with themselves. Among these groups, exemplary mention may be made of:
ureidopyrimidones;
ureidopyridines, or carbamoylpyridines;
acylamino-s-triazines, such as acyl(diamino)-s-triazines;
ureidotriazines;
phthalhydrazides;
compounds of formulae:

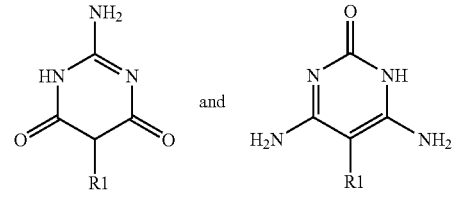

wherein the $R_1$, $R_2$ and $R_3$ radicals have the meanings given above.

Mention may also be made as examples of group capable of forming at least three H-bonds, of groups derived from ureidopyrimidones, such as 2-ureidopyrimidone or 6-methyl-2-ureidopyrimidone.

The residue of the at least one graft is constituted of a linker L carrying at least one reactive group capable of reacting with the at least one functionalized poly(alkene) group.

This at least one reactive group may, for example, be a carboxyl group or an isocyanate group. For example, it may chosen from —N=C=O and —N=C=S groups, and in at least one embodiment, —N=C=O (isocyanate) groups.

For example, the linker L may be chosen from phenylene; 1,4-nitrophenyl; 1,2-ethylene; 1,6-hexylene; 1,4-butylene; 1,6-(2,4,4-trimethylhexylene); 1,4-(4-methylpentylene); 1,5-(5-methylhexylene); 1,6-(6-methylheptylene); 1,5-(2,2,5-trimethylhexylene); 1,7-(3,7-dimethyloctylene); -isophorone-; 4,4'-methylenebiscyclohexylene; tolylene; 2-methyl-1,3-phenylene; 4-methyl-1,3-phenylene; and 4,4-biphenylenemethylene;

and by way of further example, from -isophorone-; —(CH$_2$)$_2$—; —(CH$_2$)$_6$—; —CH$_2$CH(CH$_3$)—CH$_2$—C(CH$_3$)$_2$—CH$_2$—CH$_2$; 4,4'-methylenebiscyclohexylene; and 2-methyl-1,3-phenylene.

In at least one embodiment, the at least one graft is chosen from entities of formula (B):

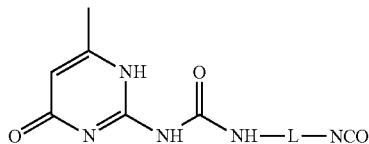

L having the same meaning as above.

In another embodiment, the supramolecular polymer of the disclosure is chosen from compounds of formula (C):

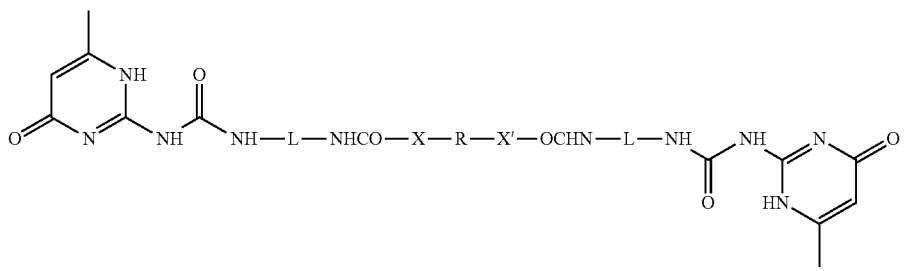
(C)

R, X, X' and L having the meanings indicated above.

In at least one embodiment, in formula (C), X and X' denote an oxygen atom.

The polyalkene-based supramolecular polymer(s) of the disclosure may also be obtained by condensing at least one polymer (A1) comprising a polyalkene part, the at least one polymer (A1) being functionalized with at least one reactive group (B1), with at least one molecule (A3) comprising at least one reactive group (B2), the at least one molecule (A3) being such that, after reaction of the at least one reactive group (B1) and and the at least one (B2) group, an entity capable of forming at least three H-bonds, such as at least four H-bonds, is formed.

In at least one embodiment, these entities have the structures (i) to (xxiv) as defined above with R$_1$ denoting a single bond.

For example, the at least one polymer (A1) may result from the action, on a polyalkene polymer of formula A as defined above, of compounds (A2) comprising two reactive groups (B'2) capable of reacting with the functionalized groups of the polyalkene.

These reactive groups may, for example, be carboxyl groups or isocyanate groups. For instance, they may be chosen from —N=C=O and —N=C=S groups, such as —N=C=O(isocyanate) groups.

In at least one embodiment, the B2 groups are identical to the B'2 groups.

In another embodiment, the compounds (A2) are of formula (C') below:

the linker L having the same meanings as L defined above.

In at least one embodiment, the at least one polymer A1 is chosen from compounds of formula (C1):

wherein L, X, X' and R have the same meanings as above.

In another embodiment, the at least one molecule (A3) is 6-methylisocytosine of formula:

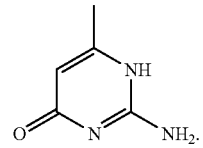

In practice, the supramolecular polymer(s) according to the disclosure may be prepared via the processes normally used by those skilled in the art for forming a urethane bond, between the free OH functions of a polyhydroxylated polyalkene and the isocyanate functions carried by the joining group. By way of illustration, and not by way of limitation, a general preparation process may comprise:

- making sure that the polymer to be functionalized does not comprise any additional water;
- heating the polymer comprising at least two reactive functions, such as at least one OH, to a temperature that may range from 60° C. to 140° C. The hydroxyl number of the polymer may act as a reference in order to measure the state of progression of the reaction;
- adding, directly, the at least one graft carrying the reactive functions, such as isocyanate;
- stirring the mixture, under a controlled atmosphere, at a temperature ranging from 90 to 130° C., for a time ranging from 1 to 24 hours;
- monitoring, by infrared spectroscopy, the disappearance of the band characteristic of the isocyanates (between 2500 and 2800 cm$^{-1}$), so as to halt the reaction at the complete disappearance of the peak, and then allowing the final product to return to ambient temperature;

the reaction may also be monitored by quantitative determinations of the hydroxyl functions;

it is also possible to optionally add ethanol in order to make sure that the residual isocyanate functions have completely disappeared;

the mixture may optionally be filtered.

The reaction can be carried out in the presence of a solvent, such as methyltetrahydrofuran, tetrahydrofuran, toluene or butyl acetate, or else propylene carbonate.

It is also possible to add a catalyst conventional for the formation of the urethane bond. By way of example, mention may be made of dibutyltin dilaurate.

At the end, the compound may be washed and dried, or even purified, according to the general knowledge of those skilled in the art.

According to another embodiment, the reaction may comprise the following stages:

(i) functionalizing at least one predried polyhydroxylated polyalkene polymer P with at least one diisocyanate according to the following reaction scheme:

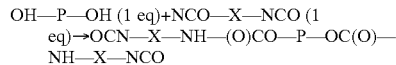

OH—P—OH (1 eq)+NCO—X—NCO (1 eq)→OCN—X—NH—(O)CO—P—OC(O)—NH—X—NCO

The at least one diisocyanate may optionally be in excess relative to the polymer. This first stage can be carried out in the presence of a solvent, at a temperature ranging from 20° C. to 100° C.

For example, this first stage can be followed by a period of stirring, under a controlled atmosphere, for a time ranging from 1 to 24 hours. The mixture may optionally be heated.

The state of progression of this first stage can be monitored by quantitative determination of the hydroxyl functions; then (ii) reacting the prepolymer obtained in stage (i) with 6-methylisocytosine according to the following reaction scheme:

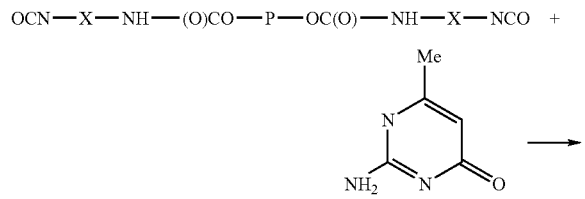

OCN—X—NH—(O)CO—P—OC(O)—NH—X—NCO +

This second stage may be optionally carried out in the presence of a cosolvent such as toluene, butyl acetate or else propylene carbonate. For example, the reaction mixture can be heated at a temperature ranging from 80° C. to 140° C. for a period of time ranging from 1 to 24 hours.

The presence of a catalyst may promote the obtaining of the desired final product. Mention may be made, for example, of the use of dibutyltin dilaurate.

The reaction can be monitored by infrared spectroscopy, by monitoring the disappearance of the peak characteristic of the isocyanate between 2200 and 2300 cm$^{-1}$.

At the end of the reaction, ethanol can be added to the reaction medium in order to neutralize the residual isocyanate functions. The reaction mixture can optionally be filtered. For application needs, the polymer may be directly stripped in a cosmetic solvent.

The polyalkene-based supramolecular polymer(s) may be present in the composition in an amount ranging from 0.1% to 40% by weight relative to the total weight of the composition, for example ranging from 0.1% to 30% by weight, or for example ranging from 0.5% to 20% by weight, or for example ranging from 1% to 15% by weight.

Pigments

The composition comprises at least one pigment. Such a composition can make it possible to obtain colored and fast coatings, without degradation of the keratin fibers.

As used herein, the term "pigment" is intended to mean any pigments contributing color to keratin substances. Their solubility in water at 25° C. and at atmospheric pressure (760 mmHg) is less than 0.05% by weight relative to the total weight of the composition, for example less than 0.01%.

The pigments which can be used include those chosen from organic and inorganic pigments known in the art, for example those which are described in Kirk-Othmer's Encyclopaedia of Chemical Technology and in Ullmann's Encyclopaedia of Industrial Chemistry.

These pigments may be in the form of a pigment powder or pigment paste. They may be coated or uncoated.

The at least one pigment may, for example, be chosen from inorganic pigments, organic pigments, lakes, special-effect pigments such as pearlescent agents or glitter, and mixtures thereof.

The at least one pigment may be an inorganic pigment. As used herein, the term "inorganic pigment" is intended to mean any pigment which corresponds to the definition of Ullmann's Encyclopaedia in the "Inorganic Pigment" chapter. Among the inorganic pigments that are of use in the present disclosure, mention may be made, for example, of iron or chromium oxides, manganese violet, ultramarine blue, chromium hydrate, ferric blue and titanium oxide.

The at least one pigment may be an organic pigment. As used herein, the term "organic pigment" is intended to mean any pigment which corresponds to the definition of Ullmann's Encyclopaedia in the "Organic Pigment" chapter. In one embodiment, the at least one organic pigment is chosen from nitroso, nitro, azo, xanthene, quinoline, anthraquinone or phthalocyanin compounds; compounds of metal complex type; and isoindolinone, isoindoline, quinacridone, perinone, perylene, diketopyrrolopyrrole, thioindigo, dioxazine, triphenylmethane and quinophthalone compounds.

For example, white or colored organic pigments may be chosen from carmine, carbon black, aniline black, azo yellow, quinacridone, phthalocyanin blue, sorghum red, the blue pigments codified in the Color Index under the references CI-42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI-61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, and the pigments obtained by oxidative polymerization of indole or phenol derivatives, such as described in French Patent No. FR 2 679 771.

The pigments in accordance with the disclosure may also be in the form of composite pigments, as described, for example, in European Patent No. EP 1 184 426. These composite pigments may be composed, for example, of particles comprising an inorganic core, at least one binder providing attachment of the organic pigments to the core, and at least one organic pigment which at least partially covers the core.

The organic pigment may also be a lake. As used herein, the term "lake" is intended to mean dyes adsorbed onto insoluble particles, the combination thus obtained remaining insoluble during use.

The inorganic substrates onto which the dyes are adsorbed are, for example, alumina, silica, calcium sodium borosilicate, calcium aluminium borosilicate and aluminium.

Exemplary mention may be made, among the dyes, of cochineal carmine. Mention may also be made of the dyes known under the following names: D & C Red 21 (CI 45 380), D & C Orange 5 (CI 45 370), D & C Red 27 (CI 45 410), D & C Orange 10 (CI 45 425), D & C Red 3 (CI 45 430), D & C Red 4 (CI 15 510), D & C Red 33 (CI 17 200), D & C Yellow 5 (CI 19 140), D & C Yellow 6 (CI 15 985), D & C Green (CI 61 570), D & C Yellow 10 (CI 77 002), D & C Green 3 (CI 42 053), D & C Blue 1 (CI 42 090).

By way of example of lakes, non-limiting mention may be made of the product known under the following name: D & C Red 7 (CI 15 850:1).

In one embodiment, the at least one pigment can also be a special-effect pigment. As used herein, the term "special-effect pigments" is intended to mean pigments which generally create a colored appearance (characterized by a certain hue, a certain vividness and a certain lightness) which is not uniform and which changes as a function of the conditions of observation (light, temperature, angles of observations, etc.). They thereby contrast with colored pigments, which provide a conventional opaque, semitransparent or transparent uniform color.

There exist several types of special-effect pigments, for example those with a low refractive index, such as fluorescent, photochromic or thermochromic pigments, and those with a greater refractive index, such as pearlescent agents or glitter.

Mention may be made, as examples of special-effect pigments, of pearlescent pigments, such as titanium oxide-coated mica covered with iron oxide, mica covered with iron oxide, mica covered with bismuth oxychloride, titanium oxide-coated mica coated with chromium oxide, titanium oxide-coated mica covered with an organic dye, such as an organic dye of the abovementioned type, and also pearlescent pigments based on bismuth oxychloride. They can also, for example, be mica particles, at the surface of which at least two successive layers of metal oxides and/or of organic coloring materials are superimposed.

In one embodiment, the pearlescent agents have a yellow, pink, red, bronze, orangey, brown, gold and/or coppery color or glint.

By way of illustration of pearlescent agents that can be used in the context of the present disclosure, exemplary mention may be made of pearlescent agents of gold color, sold for example by Engelhard under the name GOLD 222C (CLOISONNE®), SPARKLE GOLD (TIMICA®), GOLD 4504 (CHROMALITE®) and MONARCH GOLD 233X (CLOISONNE®); bronze pearlescent agents, sold for example by Merck under the names BRONZE FINE (17384) (COLORONA®) and BRONZE (17353) (COLORONA®), by Eckart under the name PRESTIGE BRONZE and by Engelhard under the name SUPER BRONZE (CLOISONNE®); orange pearlescent agents, sold far example by Engelhard under the names ORANGE 363C (CLOISONNE®) and ORANGE MCR 101 (COSMICA) and by Merck under the names PASSION ORANGE (COLORONA®) and MATTE ORANGE (17449) (MICRONA®); brown-colored pearlescent agents, sold for example by Engelhard under the names NU ANTIQUE COPPER 340XB (CLOISONNE®) and BROWN CL4509 (CHROMALITE®); pearlescent agents with a copper glint, sold for example by Engelhard under the name COPPER 340A (TIMICA®) and by Eckart under the name PRESTIGE COPPER; pearlescent agents with a red glint, sold for example by Merck under the name SIENNA FINE (17386) (COLORONA®); pearlescent agents with a yellow glint, sold for example by Engelhard under the name YELLOW (4502) (CHROMALITE®); red-coloured pearlescent agents with a gold glint, sold for example by Engelhard under the name SUNSTONE G012 (GEMTONE); black pearlescent agents with a gold glint sold, for example by Engelhard under the name NU ANTIQUE BRONZE 240 AB (TIMICA®); blue pearlescent agents sold, for example by Merck under the name MATTE BLUE (17433) (MICRONA®) or DARK BLUE (117324) (COLORONA®); white pearlescent agents with a silvery glint sold, for example by Merck under the name XIRONA® SILVER; and golden green pinkish orangey pearlescent agents sold, for example by Merck under the name INDIAN SUMMER (XIRONA®); and mixtures thereof.

In addition to pearlescent agents on a mica support, it is possible to envisage multilayer pigments based on synthetic substrates, such as alumina, silica, calcium sodium borosilicate, calcium aluminium borosilicate and aluminium.

Mention may also be made of pigments with an interference effect which are not attached to a substrate, such as liquid crystals (HELICONES HC from Wacker), or interference holographic glitter (GEOMETRIC PIGMENTS or SPECTRA f/x from Spectratek). Special effect pigments may also comprise fluorescent pigments, whether substances which are fluorescent in daylight or which produce ultraviolet fluorescence, phosphorescent pigments, photochromic pigments, thermochromic pigments and quantum dots, for example sold by Quantum Dots Corporation.

The variety of the pigments which can be used in the present disclosure may make it possible to obtain a rich palette of colors as well as specific optical effects, such as interference, metallic effects.

In one embodiment, the size of the at least one pigment used in the cosmetic composition according to the present disclosure ranges from 10 nm to 200 μm, for example from 20 nm to 80 μm, or for example from 30 nm to 50 μm.

In another embodiment, the at least one pigment can be dispersed in the product by virtue of at least one dispersing agent.

The at least one dispersing agent serves to protect the dispersed particles from the agglomeration or flocculation thereof. This dispersing agent can, for example, be a surfactant, an oligomer, a polymer, or a mixture thereof carrying at least one functionality having a strong affinity for the surface of the particles to be dispersed. In at least one embodiment, they can become attached physically or chemically to the surface of the pigments. These dispersants additionally exhibit at least one functional group compatible with or soluble in the continuous medium. Use may be made, for example, of esters of 12-hydroxystearic acid, and of $C_8$ to $C_{20}$ fatty acid and of polyol, such as glycerol or diglycerol, for example the stearate of poly(12-hydroxystearic acid) with a molecular weight of 750 g/mol, such as that sold under the name of SOLSPERSE® 21000 by Avecia, polyglyceryl-2 dipolyhydroxystearate (CTFA name), sold under the reference DEHYMYLS PGPH by Henkel, or polyhydroxystearic acid, such as that sold under the reference ARLACEL® P100 by Uniqema, and mixtures thereof.

Exemplary mention may be made, as other dispersant which can be used in the compositions of the disclosure, of the quaternary ammonium derivatives of polycondensed fatty acids, such as SOLSPERSE® 17000, sold by Avecia, and polydimethylsiloxane/oxypropylene mixtures, such as those sold by Dow Corning under the references DC2-5185 and DC2-5225 C.

The pigments used in the cosmetic composition according to the disclosure can be surface-treated with at least one organic agent.

Thus, the surface-pretreated pigments that are of use in the context of the disclosure may include pigments which have been completely or partially subjected to a surface treatment of chemical, electronic, electrochemical, mechanicochemical or mechanical nature, with at least one organic agent, such as those described, for example, in Cosmetics and Toiletries, February 1990, Vol. 105, p. 53-64, before being dispersed in the composition in accordance with the disclosure. These organic agents may, for example, be chosen from amino acids; waxes, for example carnauba wax and beeswax; fatty acids, fatty alcohols and their derivatives, such as stearic acid, hydroxystearic acid, stearyl alcohol, hydroxystearyl alcohol, lauric acid and their derivatives; anionic surfactants; lecithins; sodium, potassium, magnesium, iron, titanium, zinc or aluminium salts of fatty acids, for example aluminium stearate or aluminium laurate; metal alkoxides; polysaccharides, for example chitosan, cellulose and its derivatives; polyethylene; (meth)acrylic polymers, for example poly(methyl methacrylate)s; polymers and copolymers comprising acrylate units; proteins; alkanolamines, silicone compounds, for example silicones, polydimethylsiloxanes, alkoxysilanes, alkylsilanes or siloxysilicates; fluorinated organic compounds, for example perfluoroalkyl ethers; fluorosilicone compounds; and mixtures thereof.

In at least one embodiment, the surface-treated pigments that are of use in the cosmetic composition according to the disclosure may also have undergone at least one surface treatment, for example several surface treatments.

The surface-treated pigments that are of use in the context of the present disclosure may be prepared according to surface-treatment techniques known to those skilled in the art or found as such commercially.

For example, the surface-treated pigments can be covered with an organic layer.

The organic agent with which the pigments are treated can, for example, be deposited on the pigments by evaporation of solvent, chemical reaction between the molecules of the surface agent or creation of a covalent bond between the surface agent and the pigments.

The surface treatment may thus be carried out, for example, by chemical reaction of a surface agent with the surface of the pigments and creation of a covalent bond between the surface agent and the pigments or fillers. This method is, for example, described in U.S. Pat. No. 4,578,266.

In at least one embodiment, use is made of at least one organic agent covalently bonded to the pigments.

The at least one agent for the surface treatment is present in an amount ranging from 0.1% to 50% by weight relative to the total weight of the surface-treated pigments, for example from 0.5% to 30% by weight, or for example from 1% to 10% by weight.

For example, the surface treatments of the pigments can be chosen from:

PEG-silicone treatments, such as the AQ surface treatment marketed by LCW;
chitosan treatments, such as the CTS surface treatment marketed by LCW;
triethoxycaprylylsilane treatments, such as the AS surface treatment marketed by LCW;
methicone treatments, such as the SI surface treatment marketed by LCW;
dimethicone treatments, such as the COVASIL 3.05 surface treatment marketed by LCW;
dimethicone/trimethylsiloxysilicate treatments, such as the COVASIL 4.05 surface treatment marketed by LCW;
lauroyl lysine treatments, such as the LL surface treatment marketed by LCW;
lauroyl lysine dimethicone treatments, such as the LL/SI surface treatment marketed by LCW;
magnesium myristate treatments, such as the MM surface treatment marketed by LCW;
aluminium dimyristate treatments, such as the MI surface treatment sold by Miyoshi;
perfluoropolymethylisopropyl ether treatments, such as the FHC surface treatment marketed by LCW;
isostearyl sebacate treatments, such as the HS surface treatment marketed by Miyoshi;
disodium stearoyl glutamate treatments, such as the NAI surface treatment marketed by Miyoshi;
dimethicone/disodium stearoyl glutamate treatments, such as the SA/NAI surface treatment marketed by Miyoshi;
perfluoroalkyl phosphate treatments, such as the PF surface treatment marketed by Daito;
acrylate/dimethicone copolymer and perfluoroalkyl phosphate treatments, such as the FSA surface treatment marketed by Daito;
polymethylhydrogenosiloxane/perfluoroalkyl phosphate treatments, such as the FS01 surface treatment marketed by Daito;
lauroyl lysine/aluminium tristearate treatments, such as the LL-StAl surface treatment marketed by Daito;
octyltriethylsilane treatments, such as the OTS surface treatment marketed by Daito;
octyltriethylsilane/perfluoroalkyl phosphate treatments, such as the FOTS surface treatment marketed by Daito;
acrylate/dimethicone copolymer treatments, such as the ASC surface treatment marketed by Daito;
isopropyl titanium triisostearate treatments, such as the ITT surface treatment marketed by Daito;
microcrystalline cellulose and carboxymethylcellulose treatments, such as the AC surface treatment marketed by Daito;
cellulose treatments, such as the C2 surface treatment marketed by Daito;
acrylate copolymer treatments, such as the APD surface treatment marketed by Daito; and
perfluoroalkyl phosphate/isopropyl titanium triisostearate treatments, such as the PF+ITT surface treatment marketed by Daito.

The composition in accordance with the present disclosure may also comprise at least one pigment that is not surface-treated.

According to at least one embodiment of the disclosure, the at least one pigment is an inorganic pigment.

According to another embodiment of the disclosure, the at least one pigment is chosen from pearlescent agents.

In at least one embodiment, the at least one pigment is present in an amount ranging from 0.5% to 40% relative to the total weight of the composition, for example from 1% to 20%.

The composition of the disclosure may comprise at least one other colored and/or coloring substances, such as hydrophilic or hydrophobic direct dyes, or dye precursors.

Volatile Solvents

The composition in accordance with the disclosure comprises at least one volatile solvent.

As used herein, the term "volatile solvent" is intended to mean a compound that is liquid at ambient temperature (20° C.) and at atmospheric pressure and which has a vapor pressure at 20° C. of greater than 0.1 mmHg, for example ranging from 0.1 to 300 mmHg, or for example ranging from 0.5 and 200 mmHg.

The at least one volatile solvent may be chosen from water, non-silicone organic solvents, silicone organic solvents, and mixtures thereof. By way of volatile non-silicone organic solvents, exemplary mention may be made of:

$C_1$-$C_4$ volatile alkanols, such as ethanol or isopropanol;

$C_5$-$C_7$ volatile alkanes, such as n-pentane, hexane, cyclopentane, 2,3-dimethylbutane, 2,2-dimethylbutane, 2-methylpentane or 3-methylpentane;

esters of liquid $C_1$-$C_{20}$ acids and of $C_1$-$C_8$ alcohols that are volatile, such as methyl acetate, n-butyl acetate, ethyl acetate, propyl acetate, isopentyl acetate or ethyl 3-ethoxypropionate;

ketones that are liquid at ambient temperature and volatile, such as methyl ethyl ketone, methyl isobutyl ketone, diisobutyl ketone, isophorone, cyclohexanone or acetone;

volatile ethers, such as dimethoxymethane, diethoxyethane or diethyl ether;

volatile glycol ethers, such as 2-butoxyethanol, butyl diglycol, diethylene glycol monomethyl ether, propylene glycol n-butyl ether, or propylene glycol monomethyl ether acetate;

volatile hydrocarbon-based oils, such as volatile hydrocarbon-based oils containing from 8 to 16 carbon atoms, and mixtures thereof, such as $C_8$-$C_{16}$ branched alkanes, for instance $C_8$-$C_{16}$ isoalkanes (also known as isoparaffins), isododecane or isodecane, and, for example, the oils sold under the trade names ISOPARS or PERMETYLS, or mixtures thereof. Exemplary mention may also be made of isohexyl neopentanoate or isodecyl neopentanoate;

$C_4$-$C_{10}$ volatile perfluoroalkanes, such as dodecafluoropentane, tetradecafluorohexane or decafluoropentane;

volatile perfluorocycloalkyls, such as perfluoromethylcyclopentane, 1,3-perfluorodimethylcyclohexane and perfluorodecaline, sold respectively under the names FLUTEC PC1®, FLUTEC PC3® and FLUTEC PC6® by the company F2 Chemicals, and also polyfluorodimethylcyclobutane and perfluoromorpholine;

volatile fluoroalkyl or heterofluoroalkyl compounds corresponding to the formula:

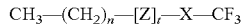

$$CH_3-(CH_2)_n-[Z]_t-X-CF_3$$

wherein t is 0 or 1; n is 0, 1, 2 or 3; X is a linear or branched, divalent perfluoroalkyl radical containing from 2 to 5 carbon atoms, and Z is chosen from O, S and NR, R being hydrogen or a —$(CH_2)_n$—$CH_3$ or —$(CF_2)_m$—$CF_3$ radical, m being 2, 3, 4 or 5.

Among the volatile fluoroalkyl or heterofluoroalkyl compounds, exemplary mention may be made of methoxynonafluorobutane sold under the name MSX 4518® and HFE-7100® by the company 3M, and ethoxynonafluorobutane sold under the name HFE-7200® by the company 3M.

In at least one embodiment, the solvent is chosen in such a way that the boiling point thereof is below 200° C.

According to at least one embodiment, the non-silicone organic solvent is chosen from ethanol, isopropanol, acetone and isododecane.

By way of volatile silicone solvent, exemplary mention may be made of silicone compounds with a low viscosity, chosen from linear or cyclic silicones containing from 2 to 7 silicon atoms, these silicones optionally comprising alkyl or alkoxy groups containing from 1 to 10 carbon atoms, such as octamethylcyclotetrasiloxane, decamethylcyclopentasiloxane, dodecamethylcyclohexasiloxane, heptamethylhexyltrisiloxane, heptamethylethyltrisiloxane, octamethyltrisiloxane, decamethyltetrasiloxane, and mixtures thereof.

According to at least one embodiment, the silicone compound is chosen from cyclopentadimethylsiloxane, dodecamethylcyclohexasiloxane, octamethyltrisiloxane and decamethyltetrasiloxane.

By way of example, mention may be made of the decamethylcyclopentasiloxane sold under the name DC-245 by the company Dow Corning, the octamethyltrisiloxane sold under the name DC-200 Fluid 1 cst by the company Dow Corning and the decamethyltetrasiloxane sold under the name DC-200 FLUID 1.5 cst by the company Dow Corning.

According to at least one embodiment of the disclosure, the at least one volatile solvent is chosen from water, ethanol, isopropanol, acetone, isododecane, decamethylcyclopentasiloxane, octamethyltrisiloxane and decamethyltetrasiloxane.

The at least one volatile solvent may be present in the composition that is of use in the process of the disclosure in an amount ranging from 0.1% to 95% by weight, relative to the total weight of the composition, for example ranging from 1% to 90% by weight, or for example ranging from 5% to 90% by weight.

Other Solvents

The composition of the invention may also comprise at least one non-volatile organic solvent, such as:

non-volatile aromatic alcohols, such as benzyl alcohol or phenoxyethanol;

esters of liquid $C_1$-$C_{20}$ acids and of $C_1$-$C_8$ alcohols that are non-volatile, such as isopropyl myristate;

ethylene carbonate, propylene carbonate, butylene carbonate;

non-volatile polyols, such as glycerol, ethylene glycol, dipropylene glycol or butylene glycol;

non-volatile glycol ethers, for instance diethylene glycol monoethyl ether or dipropylene glycol mono-n-butyl ether;

non-volatile hydrocarbon-based oils, such as isohexadecane;

$C_{10}$-$C_{30}$ non-volatile liquid fatty alcohols, such as oleyl alcohol, liquid $C_{10}$-$C_{30}$ fatty alcohol esters, such as $C_{10}$-$C_{30}$ fatty alkyl benzoates, and mixtures thereof; polybutene oil, isononyl isononanoate, isostearyl malate, pentaerythrityl tetraisostearate, tridecyl trimellate;

non-volatile perfluoro solvents, such as perfluoroperhydrophenanthrene, sold under the name FLUTEC PC11® by the company F2 Chemicals;

non-volatile silicones with a low viscosity, such as the polydimethylsiloxane with a viscosity of 5 cst sold by Dow Corning under the name DOW CORNING 200 FLUID 5 cst, and the polydimethylsiloxane with a viscosity of 10 cst sold by Dow Corning under the name DOW CORNING 200 FLUID 10 cst.

Additional Silicone Compounds

In order to obtain better spreading of the composition of the disclosure and also improved coating, the composition of the disclosure may also comprise at least one silicone compound chosen from polysiloxanes having a viscosity of greater than 100 cst, for example greater than 300 cst. The viscosity of the at least one polysiloxane can be measured according to ASTM standard D-445. For example, such polysiloxane may be chosen from silicone oils, gums or resins, and crosslinked silicones.

By way of polysiloxanes with a viscosity of greater than 100 cst, exemplary mention may be made of polydimethylsiloxanes; alkyl dimethicones; poly-phenylmethylsiloxanes, such as phenyl dimethicones, phenyl trimethicones and vinyl-methyl methicones; and also silicones modified with aliphatic and/or aromatic groups, which are optionally fluorinated, or with functional groups such as hydroxyl, thiol and/or amine groups.

In one embodiment, such polysiloxanes are chosen from the silicones of formula (I):

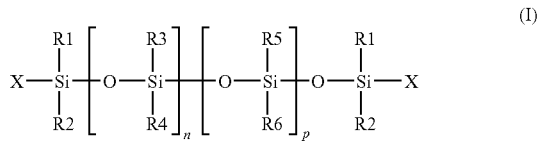

wherein:

$R_1$, $R_2$, $R_5$ and $R_6$ are, together or separately, chosen from alkyl radicals containing 1 to 6 carbon atoms, $R_3$ and $R_4$ are, together or separately, chosen from alkyl radicals containing from 1 to 6 carbon atoms, vinyl radicals, aryl radicals, aminoalkyl radicals containing from 1 to 6 carbon atoms, which are optionally substituted, hydroxyl radicals and thioalkyl radicals containing from 1 to 6 carbon atoms, and X is chosen from alkyl radicals containing from 1 to 6 carbon atoms, hydroxyl radicals, vinyl radicals, aminoalkyl radicals containing from 1 to 6 carbon atoms, which are optionally substituted, and thioalkyl radicals containing from 1 to 6 carbon atoms, n and p being integers chosen so as to obtain a viscosity of greater than 300 cst.

By way of example, mention may be made of the following polydimethylsiloxanes:
- the substituents $R_1$ to $R_6$ and X represent a methyl group, such as the product sold under the name BAYSILICONE TP 3898 by the company General Electric, and the product sold under the name AK 500000 by the company Wacker,
- the substituents $R_1$ to $R_6$ and X represent a methyl group, p and n are such that the molecular weight is 120,000 g/mol, such as the product sold under the name DOW CORNING 200 FLUID 60000 CS by the company Dow Corning,
- the substituents $R_1$ to $R_6$ and X represent a methyl group, p and n are such that the molecular weight is 250,000 g/mol, such as the product sold under the name MIRASIL DM 500.000 by the company Rhodia, and the product sold under the name DOW CORNING 200 FLUID 500.000 cst by the company Dow Corning,
- the substituents $R_1$ to $R_6$ represents a methyl group, the group X represents a hydroxyl group, n and p are such that the molecular weight of the polymer is 600,000 g/mol, such as the product sold under the name SGM 36 by the company Dow Corning,
- dimethicones of the (polydimethylsiloxane)(methylvinylsiloxane) type, such as SE63 sold by GE Bayer Silicones, poly(dimethylsiloxane)(diphenyl)(methylvinylsiloxane) copolymers,
- and mixtures thereof.

When the at least one polysiloxane comprises a fluoro group, the copolymers may, for example, be chosen from those having the following structure:

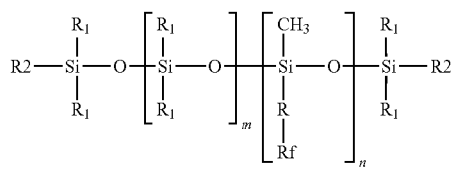

wherein:

R is chosen from divalent, linear and/or branched alkyl groups containing 1 to 6 carbon atoms, such as a methyl, ethyl, propyl or butyl divalent group, Rf represents a fluoroalkyl radical, for example a perfluoroalkyl radical, containing from 1 to 12 carbon atoms, such as from 1 to 9 carbon atoms, $R_1$ is chosen from, independently of one another, $C_1$-$C_{20}$ alkyl radicals, hydroxyl radicals and phenyl radicals, $R_2$ represents $R_1$ or Rf, m is a number ranging from 0 to 500, for example from 0 to 200, and n is a number ranging from 1 to 1,000, for example from 1 to 500.

In at least one embodiment, the $R_1$ groups are identical and represent a methyl radical.

Such polysiloxanes include, for example, those sold by the company Shin Etsu under the names FL-5, FL-10, X22-821 and X22-822, or FL-100, by the company Dow Corning under the name FS-1265 FLUID, or by the company Phoenix Chemical under the PECOSIL® FS range, under the names PECOSIL® FSL-150, PECOSIL® FSL-300, PECOSIL® FSH-150, PECOSIL® FSH-300, PECOSIL® FSU-150 and PECOSIL® FSU-300.

In one embodiment, the weight-average molecular mass of the at least one polysiloxane may range from 1,000 to 1,500,000 g/mol, for example from 20,000 to 1,000,000 g/mol.

In one embodiment, the at least one polysiloxane may be in the form of a resin. As used herein, the term "resin" is intended to mean a crosslinked or noncrosslinked three-dimensional structure. By way of example of a polysiloxane resin, mention may be made of silsesquioxanes and siloxysilicates.

The nomenclature of silicone resins is known as "MDTQ", the resin being described as a function of the various siloxane monomeric units that it comprises, each of the letters "MDTQ" characterizing a type of unit.

The letter M represents the monofunctional unit of formula $(CH_3)_3SiO_{1/2}$, the silicon atom being linked to a single oxygen atom in the polymer comprising this unit.

The letter D signifies a difunctional $(CH_3)_2SiO_{2/2}$ unit in which the silicon atom is linked to two oxygen atoms.

The letter T represents a trifunctional unit of formula $(CH_3)SiO_{3/2}$.

In at least one embodiment, in the M, D and T units defined above, at least one of the methyl groups can be substituted with a group R different from the methyl group, such as a hydrocarbon-based (such as alkyl) radical containing from 2 to 10 carbon atoms or a phenyl group or alternatively a hydroxyl group.

Finally, the letter Q signifies a tetrafunctional $SiO_{4/2}$ unit wherein the silicon atom is linked to four hydrogen atoms, themselves linked to the rest of the polymer.

Various resins having different properties can be obtained from these various units, the properties of these polymers varying according to the type of monomers (or units), to the type and number of radicals substituted, to the length of the polymer chain, to the degree of branching and to the size of the pendent chains.

By way of example of these silicone resins, mention may be made of:
- siloxysilicates which can be trimethylsiloxysilicates of formula $[(CH_3)_3SiO]_x(SiO_{4/2})_y$ (MQ units) wherein x and y are integers ranging from 50 to 80,
- polysilsesquioxanes of formula $(CH_3SiO_{3/2})_x$ (T units) wherein at least one of the methyl radicals can be substituted with a group R as defined above. In at least one embodiment, the number x of T units of the silsesquioxane is less than or equal to 500, for example the number x of T units may range from 50 to 500. In at least one embodiment, the molecular weight of the silicone resin(s) according to the disclosure ranges from 500 to 50,000 g/mol, for example from 500 to 20,000 g/mol, or for example from 500 to 10,000 g/mol;

polymethylsilsesquioxanes which are polysilsesquioxanes wherein none of the methyl radicals are substituted with another group. Such polymethylsilsesquioxanes are described, for example, in U.S. Pat. No. 5,246,694;

polypropylsilsesquioxanes, wherein the methyl radicals are replaced with propyl radicals. These compounds, and also the synthesis thereof, are for example described in International Patent Application WO 2005/075567;

polyphenylsilsesquioxanes, wherein the methyl radicals are replaced with phenyl radicals. These compounds, and also the synthesis thereof, are for example described in U.S. Patent Application Publication No. 2004/0180011.

By way of examples of commercially available polymethylsilsesquioxane resins, mention may be made of those which are marketed:

by the company Wacker under the reference RESIN MK, such as BELSIL® PMS MK: polymer comprising repeating $CH_3SiO_{3/2}$ units (T units) that may also comprise up to 1% by weight of $(CH_3)_2SiO_{2/2}$ units (D units) and that has an average molecular weight of 10,000 g/mol. It is thought that the polymer is in a "cage" and "ladder" configuration as is represented in the figures below. The average molecular weight of the units in the "cage" configuration was calculated at 536 g/mol. The majority of the polymer is in the "ladder" configuration with ethoxy groups at the ends. These ethoxy groups represent 4.5% by mass of the polymer. Since these ends can react with water, a small and variable amount of SiOH groups may also be present.

by the company Dow Corning under the reference DOW CORNING 217 FLAKE RESIN, which is a silanol-terminated polyphenylsilsesquioxane;

by the company Wacker under the reference BELSIL® SPR 45 VP.

As siloxysilicate resins, exemplary mention may be made of trimethylsiloxysilicate (TMS) resins, optionally in the form of powders. Such resins are marketed under the reference SR1000 by the company General Electric or under the reference TMS 803 by the company Wacker. Mention may also be made, for example, of the trimethylsiloxysilicate resins marketed in a solvent such as cyclomethicone, sold under the name KF-7312J by the company Shin-Etsu, and DC 749 and DC 593 by the company Dow Corning.

In at least one embodiment, the silicone resin according to the disclosure is film-forming. In fact, not all silsesquioxanes are film-forming, for example the highly polymerized polymethylsilsesquioxanes such as TOSPEARL™ from Toshiba or KMP590 from Shin-Etsu are insoluble and are not film-forming.

In at least one embodiment, the silicone resin(s) is (are) soluble or dispersible in the composition of the disclosure. In at least one embodiment, the silicone resin(s) according to the disclosure is (are) soluble in volatile silicones and organic solvents. In one embodiment, the silicone resin(s) is (are) solid at 25° C.

For example, the silicone resin(s) according to the disclosure may be chosen from trimethylsiloxysilicate resins, polymethylsilsesquioxane resins and polypropylsilsesquioxane resins.

The composition of the disclosure may also comprise at least one crosslinked silicone such as a crosslinked elastomeric organopolysiloxane, which is a high-molecular-weight

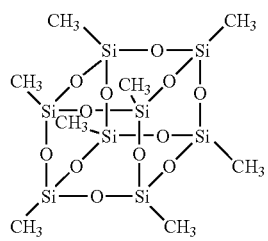

Cage

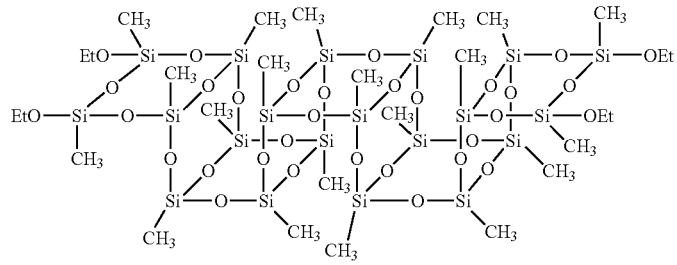

Ladder by the company Shin-Etsu under the references KR-220L, which are composed of T units of formula $CH_3SiO_{3/2}$ and have SiOH (silanol) terminal groups, under the reference KR-242A, which comprise 98% of T units and 2% of dimethyl units D and have SiOH terminal groups, or else under the reference KR-251, comprising 88% of T units and 12% of dimethyl units D and having SiOH terminal groups.

By way of examples of commercially available polypropylsilsesquioxane resins, mention may be made of those which are marketed:

by the company Dow Corning under the reference DOW CORNING 670 FLUID, which is a polypropylsilsesquioxane diluted in D5.

By way of examples of commercially available polyphenylsilsesquioxane resins, mention may be made of those which are marketed:

silicone compound having a three-dimensional structure, with the viscoelastic properties of a flexible solid material. These organopolysiloxanes may, for example, be in powdered dry form, or in swollen form, in a solvent, the resulting product generally being a gel. These products may also, for example, be in a form dispersed in an aqueous solvent.

The synthesis of these organopolysiloxanes is described in the following patents:

U.S. Pat. No. 5,266,321 to Kobayashi Kose,
U.S. Pat. No. 4,742,142 to Toray Silicone,
U.S. Pat. No. 5,654,362 to Dow Corning Corp., and
French Patent Application No. FR 2 864 784.

The elastomeric organopolysiloxanes used in the composition may be partially or totally crosslinked. They are generally in the form of particles. For example, the elastomeric organopolysiloxane particles may have a number-average size ranging from 0.1 to 500 μm. These particles may be of any shape, and, for example, may be spherical, flat or amorphous.

The crosslinked organopolysiloxane obtained may be a non-emulsifying compound or an emulsifying compound. As used herein, the term "non-emulsifying" defines crosslinked organopolysiloxanes which do not contain polyoxyalkylene units. As used herein, the term "emulsifying" signifies crosslinked organopolysiloxane compounds having at least one polyoxyalkylene, for example polyoxyethylene or polyoxypropylene, unit.

The crosslinked organopolysiloxane particles may be conveyed in the form of a gel constituted of a crosslinked organopolysiloxane included in at least one hydrocarbon-based oil and/or at least one silicone oil. In these gels, the organopolysiloxane particles are commonly non-spherical particles. The crosslinked organopolysiloxane particles may also be in the form of a powder, for example in the form of a spherical powder.

Non-emulsifying crosslinked organopolysiloxanes are, for example, described in U.S. Pat. Nos. 4,970,252, 4,987,169, 5,412,004, 5,654,362 and 5,760,116, and in Japanese Patent Application JP-A-61-194009.

As non-emulsifying crosslinked organopolysiloxanes, use may be made, for example, of those sold under the names KSG-6, KSG-15, KSG-16, KSG-18, KSG-31, KSG-32, KSG-33, KSG-41, KSG-42, KSG-43, KSG-44 and USG-103 by the company Shin-Etsu, DC 9040, DC 9041, DC 9509, DC 9505, DC 9506 and DC 9045 by the company Dow Corning, Gransil by the company Grant Industries, and SFE 839 by the company General Electric.

In at least one embodiment, the emulsifying crosslinked organopolysiloxanes comprise polyoxyalkylene-modified organopolysiloxanes formed from divinyl compounds, such as polysiloxanes having at least two vinyl groups, which react with Si—H bonds of a polysiloxane. Exemplary emulsifying crosslinked organopolysiloxanes are described in U.S. Pat. Nos. 5,236,986, 5,412,004, 5,837,793 and 5,811,487.

As emulsifying crosslinked organopolysiloxanes, use may be made, for example, of those marketed under the names KSG-21, KSG-20 and KSG-30 by the company Shin Etsu, and DC 9010 and DC 9011 by the company Dow Corning.

The particles of elastomeric crosslinked organopolysiloxane may also, for example, be in the form of a powder of elastomeric crosslinked organopolysiloxane coated with silicone resin, such as with silsesquioxane resin, as described, for example, in U.S. Pat. No. 5,538,793.

Such elastomers are sold, for example, under the names KSP-100, KSP-101, KSP-102, KSP-103, KSP-104 and KSP-105 by the company Shin Etsu.

In at least one embodiment, the crosslinked organopolysiloxane is non-emulsifying.

The composition of the disclosure may also comprise at least one grafted silicone compound. As used herein, the term "grafted silicone polymer" is intended to mean a polymer comprising a polysiloxane portion and a portion constituted of a non-silicone organic chain, one of the two portions constituting the main chain of the polymer, the other being grafted onto the main chain.

In at least one embodiment, the grafted silicone polymers used in the cosmetic composition according to the disclosure are chosen from the polymers having a non-silicone organic backbone grafted with monomers containing a polysiloxane, polymers having a polysiloxane backbone grafted with non-silicone organic monomers, and mixtures thereof.

In another embodiment, the non-silicone organic monomers constituting the main chain of the grafted silicone polymer may be chosen from free-radical-polymerizable, ethylenically unsaturated monomers, polycondensation-polymerizable monomers, such as those forming polyamides, polyesters or polyurethanes, and ring-opening monomers such as those of the oxazoline or caprolactone type.

In at least one embodiment, the polymers having a non-silicone organic backbone grafted with monomers containing a polysiloxane, in accordance with the disclosure, can be chosen from those described in U.S. Pat. Nos. 4,693,935, 4,728,571 and 4,972,037 and International Patent Applications EP-A-0 412 704, EP-A-0 412 707, EP-A-0 640 105 and WO 95/00578. They are copolymers obtained by free-radical polymerization starting from ethylenically unsaturated monomers and silicone macromers having a terminal vinyl group, or else copolymers obtained by reaction of a polyolefin comprising functionalized groups and of a polysiloxane macromer having a terminal function that is reactive with said functionalized groups.

The copolymer having a non-silicone organic backbone grafted with monomers containing a polysiloxane may, for example, have the following structure:

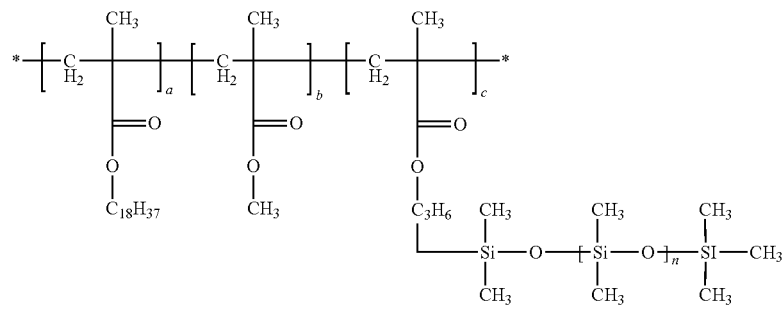

Such a polymer is marketed under the name KP 561 by Shin Etsu.

The copolymer having a non-silicone organic backbone grafted with monomers containing a polysiloxane may also have the following structure:

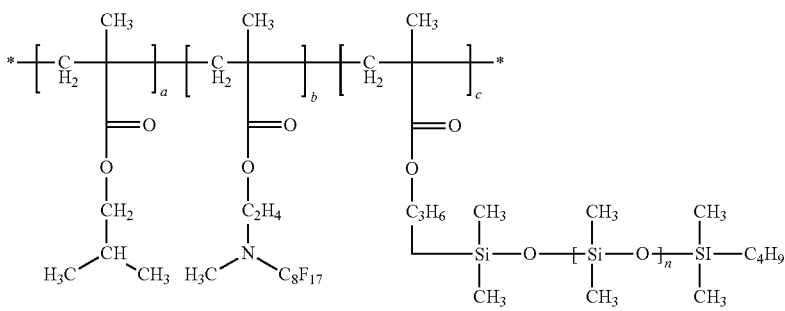

Such a polymer, Polysilicone 7, is marketed under the name SA70 by 3M.

Other copolymers having a non-silicone organic backbone grafted with monomers containing polysiloxane may, for example, be chosen from KP545, KP574 and KP575, marketed by Shin Etsu.

As a grafted silicone compound, exemplary mention may also be made of the isobutyl methacrylate/bis(hydroxypropyl) dimethicone acrylate copolymer sold by Grant Industries under the name GRANACRYSIL BMAS.

According to the present disclosure, the at least one grafted silicone polymer, having a polysiloxane backbone grafted with non-silicone organic monomers, comprises a main chain of silicone (or polysiloxane ($\equiv$Si—O—)$_n$) onto which is grafted, within said chain and also, optionally, at least one of its ends, at least one organic group which does not comprise silicone.

Non-limiting examples of such grafted silicone polymers include polydimethylsiloxanes (PDMSs) onto which are grafted, by means of a thiopropylene-type connecting chain, mixed polymer units of the poly(meth)acrylic acid type and of the poly(alkyl (meth)acrylate) type. Exemplary mention may also be made of polydimethylsiloxane or polymethylsiloxane comprising methyl 3-(propylthio)acrylate/methyl methacrylate/methacrylic acid groups, or Polysilicone-8 marketed under the name VS80 by the company 3M.

Other examples of such grafted silicone polymers are polydimethylsiloxanes (PDMSs) onto which are grafted, via a thiopropylene-type connecting chain, polymer units of the poly(isobutyl (meth)acrylate) type.

In at least one embodiment, the number-average molecular mass of the at least one silicone polymer having a polysiloxane backbone grafted with non-silicone organic monomers, of the disclosure, ranges from 10,000 to 1,000,000, for example from 10,000 to 100,000.

In at least one embodiment, the at least one grafted silicone polymer is chosen from polydimethylsiloxane-grafted alkyl methacrylate copolymer, isobutyl methacrylate/acrylic acid/silicone macromer copolymers and polydimethylsiloxane or polymethylsiloxane comprising methyl 3-(propylthio)acrylate/methyl methacrylate/methacrylic acid groups.

According to at least one embodiment, the composition of the disclosure further comprises at least one additional silicone compound chosen from polysiloxanes having a viscosity of greater than 100 cst and grafted silicone compounds.

According to at least one embodiment, the polysiloxane(s) having a viscosity greater than 100 cst is (are) chosen from polydimethylsiloxanes.

According to one another embodiment, the polysiloxane(s) having a viscosity of greater than 100 cst is (are) chosen from silicone resins.

When they are present in the composition in accordance with the disclosure, the at least one additional silicone compound(s) is (are) present in an amount ranging from 0.1% to 30% by weight relative to the total weight of the composition, for example from 0.1% to 20% by weight, or for example from 0.1% to 10% by weight.

Other Additives

When the polymer has a glass transition temperature that is too high for the desired use, at least one plasticizer may be combined therewith so as to reduce the glass transition temperature of the mixture used. The at least one plasticizer may be chosen from plasticizers normally used in the field of application, and/or may be chosen, for example, from compounds that can be solvents for the polymer.

In at least one embodiment, the at least one plasticizer has a molecular mass of less than or equal to 5,000 g/mol, for example less than or equal to 2,000 g/mol, or for example less than or equal to 1,000 g/mol. In another embodiment, the plasticizer has a molecular mass of greater than or equal to 100 g/mol.

Thus, in at least one embodiment, the composition may also comprise at least one plasticizer. Exemplary mention may be made, of the usual plasticizers, such as:
- glycols and derivatives thereof, such as diethylene glycol ethyl ether, diethylene glycol methyl ether, diethylene glycol butyl ether or else diethylene glycol hexyl ether, ethylene glycol ethyl ether, ethylene glycol butyl ether or ethylene glycol hexyl ether;
- polyethylene glycols, polypropylene glycols, polyethylene glycol/polypropylene glycol copolymers and mixtures thereof, such as high-molecular-weight polypropylene glycols having, for example, a molecular mass ranging from 500 to 15,000 g/mol, such as, for example:
- glycol esters;
- propylene glycol derivatives, such as propylene glycol phenyl ether, propylene glycol diacetate, dipropylene glycol ethyl ether, tripropylene glycol methyl ether and diethylene glycol methyl ether, and dipropylene glycol butyl ether. Such compounds are marketed, for example, by Dow Chemical under the names DOWANOL PPH and DOWANOL DPnB;
- esters of acids, for example of carboxylic acids, such as citrates, phthalates, adipates, carbonates, tartrates, phosphates or sebacates;
- esters derived from the reaction of a monocarboxylic acid of formula $R_{11}$COOH with a diol of formula HOR$_{12}$OH where $R_{11}$ and $R_{12}$, which may be identical or different, represent a saturated or unsaturated, linear, branched or cyclic, hydrocarbon-based chain for example containing from 3 to 15 carbon atoms, optionally comprising at least one heteroatom such as N, O or S, for example the monoester resulting from the reaction of isobutyric acid and octanediol, such as 2,2,4-trimethylpentane-1,3-diol, for instance the product sold under the reference TEXANOL ESTER ALCOHOL by the company Eastman Chemical;

oxyethylenated derivatives, such as oxyethylenated oils, for example plant oils, such as castor oil;

and mixtures thereof.

For example, the at least one plasticizer may be chosen from esters of at least one carboxylic acid containing from 1 to 7 carbon atoms and of a polyol comprising at least 4 hydroxyl groups.

The polyol according to the disclosure may, for example, be a cyclized or uncyclized saccharide-polyhydroxyaldehyde (aldose) or polyhydroxyketone (ketose). In at least one embodiment, the polyol is a saccharide cyclized in hemiacetal form.

The polyol may, for example, be a monosaccharide or a polysaccharide comprising from 1 to 10 saccharides, such as from 1 to 4 saccharides, or such as one or two saccharides. In at least one embodiment, the polyol may be chosen from erythritol, xylitol, sorbitol, glucose, sucrose, lactose and maltose.

In at least one embodiment, the polyol according to the disclosure is a disaccharide. Among the disaccharides, exemplary mention may be made of sucrose (also known as alpha-D-glucopyranosyl-(1-2)-beta-D-fructofuranose), lactose (also known as beta-D-galactopyranosyl-(1-4)-beta-D-glucopyranose) and maltose (also known as alpha-D-glucopyranosyl-(1-4)-beta-D-glucopyranose). In at least one embodiment, the polyol is sucrose.

The ester according to the disclosure may, for example, be constituted of a polyol esterified with at least two different monocarboxylic acids, or with at least three different monocarboxylic acids.

The ester according to the disclosure may, for example, be a copolymer of two esters, and in at least one embodiment is a copolymer i) of a sucrose substituted with benzoyl groups and ii) of a sucrose substituted with acetyl and/or isobutyryl groups.

In at least one embodiment, the carboxylic acid is a monocarboxylic acid containing from 1 to 7 carbon atoms, such as from 1 to 5 carbon atoms, chosen, for example, from acetic acid, n-propanoic acid, isopropanoic acid, n-butanoic acid, isobutanoic acid, tert-butanoic acid, n-pentanoic acid and benzoic acid.

The ester may be obtained, for example, from at least two different monocarboxylic acids. According to one embodiment, the acid is an unsubstituted linear or branched acid.

In at least one embodiment, the acid is chosen from acetic acid, isobutyric acid, benzoic acid, and mixtures thereof.

According to one embodiment, the ester is sucrose diacetate hexakis(2-methylpropanoate), such as the product sold under the name SUSTANE SAIB Food Grade Kosher by the company Eastman Chemical.

According to another embodiment, the at least one plasticizer may be chosen from esters of an aliphatic or aromatic polycarboxylic acid and of an aliphatic or aromatic alcohol containing from 1 to 10 carbon atoms.

The aliphatic or aromatic alcohol may contain, for example, from 1 to 10 carbon atoms, such as from 1 to 8, for example from 1 to 6. It may be chosen, for example, from alcohols R1OH, such that R1 represents methyl, ethyl, propyl, isopropyl, butyl, hexyl, ethylhexyl, decyl, isodecyl, benzyl or benzyl substituted with an alkyl containing 1 to 3 carbon atoms, and mixtures thereof.

In at least one embodiment, the aliphatic or aromatic polycarboxylic acid contains from 3 to 12 carbon atoms, such as from 3 to 10 carbon atoms, or such as from 3 to 8 carbon atoms, for example 6 or 8 carbon atoms.

In at least one embodiment, the aliphatic or aromatic polycarboxylic acid is chosen from dicarboxylic acids and tricarboxylic acids.

Among the aliphatic dicarboxylic acids, exemplary mention may be made of those of formula $HOOC-(CH_2)_n-COOH$, wherein n is an integer ranging from 1 to 10, for example ranging from 2 to 8, or for example equal to 2, 4, 6 or 8.

In at least one embodiment, the dicarboxylic acids are chosen from succinic acid, adipic acid and sebacic acid.

Among the aromatic dicarboxylic acids, exemplary mention may be made of phthalic acid.

Among the tricarboxylic acids, exemplary mention may be made of the triacids that correspond to the formula:

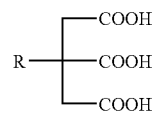

wherein R represents an —H, —OH or —OCOR' group wherein R' represents an alkyl group containing from 1 to 6 carbon atoms. In one embodiment, R represents an —OCOCH$_3$ group.

In one embodiment, the tricarboxylic acid is chosen from acetylcitric acid, butyroylcitric acid and citric acid.

Non-limiting examples of tricarboxylic acid esters that may be used are esters derived from citric acid (or citrates) such as tributyl acetyl citrate, triethyl acetyl citrate, triethylhexyl acetyl citrate, trihexyl acetyl citrate, trihexyl butyroyl citrate, triisodecyl citrate, triisopropyl citrate, tributyl citrate and tris(2-ethylhexyl) citrate. As commercial references of plasticizers mentioned above, exemplary mention may be made of the CITROFLEX range marketed by Vertellus, such as CITROFLEX A4 and CITROFLEX C2.

Among the adipic acid esters, exemplary mention may be made of dibutyl adipate and bis(2-ethylhexyl) adipate.

Among the sebacic acid esters, exemplary mention may be made of dibutyl sebacate, bis(2-ethylhexyl) sebacate, diethyl sebacate and diisopropyl sebacate.

Among the succinic acid esters, exemplary mention may be made of bis(2-ethylhexyl) succinate and diethyl succinate.

Among the phthalic acid esters, exemplary mention may be made of butyl benzyl phthalate, dibutyl phthalate, diethylhexyl phthalate, diethyl phthalate and dimethyl phthalate.

In at least one embodiment, the at least one plasticizer may be present in the composition in an amount such that the mass ratio between the at least one hydrophobic film-forming polymer and the at least one plasticizer has a value that ranges from 0.5 to 100, for example from 1 to 50, or for example from 1 to 20.

The composition according to the disclosure may comprise at least one thickener chosen from polymeric thickeners and inorganic thickeners.

The at least one thickener may be inorganic or organic, and polymeric or non-polymeric. The at least one thickener may be chosen to thicken an aqueous phase or a fatty phase of the composition, as appropriate.

As used herein, the term "thickener" is intended to mean a compound that modifies the rheology of the medium into which it is incorporated by increasing by at least 100 cps the viscosity of the medium at 25° C. and at a shear rate of 1 s$^{-1}$.

This viscosity can be measured, for example, using a cone/plate viscometer (Haake R600 rheometer, or the like).

For example, the at least one aqueous phase thickener is chosen from:
hydrophilic clays,
hydrophilic fumed silica,
water-soluble cellulose-based thickeners, such as hydroxyethylcellulose, methylcellulose and hydroxypropylcellulose. Among these, exemplary mention may be made of the gums sold under the name CELLOSIZE QP 4400H by the company Amerchol,
nonionic guar gums comprising $C_1$-$C_6$ hydroxyalkyl groups. By way of example, mention may be made of hydroxymethyl, hydroxypropyl and hydroxybutyl groups. Such guar gums are, for example, sold under the trade names JAGUAR HP8, JAGUAR HP60, JAGUAR HP120 and JAGUAR HP105 by the company Meyhall or under the name GALACTASOL 40H4FD2 by the company Aqualon,
carrageenans,
locust bean gum, scieroglucan gum, gellan gum, rhamsan gum or karaya gum,
alginates, maltodextrins, starch and derivatives thereof, and hyaluronic acid and salts thereof,
polyglyceryl (meth)acrylate polymers sold under the names HISPAGEL or LUBRAGEL by the companies Hispano Quimica or Guardian,
polyvinyl alcohol,
crosslinked acrylamide polymers and copolymers, such as those sold under the names PAS 5161 or BOZEPOL C by the company Hoechst, SEPIGEL 305 by the company Seppic by the company Allied Colloid, or
the crosslinked methacryloyloxyethyltrimethylammonium chloride homopolymers sold under the name SALCARE SC95 by the company Allied Colloid,
associative polymers, such as associative polyurethanes.

Such thickeners are, for example, described in International application EP-A-1 400 234.

For example, the at least one fatty phase thickener may be chosen from:
organophilic clays;
hydrophobic fumed silicas;
alkyl guar gums (with a $C_1$-$C_6$ alkyl group), such as those described in European Patent No. EP-A-708114;
oil-gelling polymers, for instance triblock polymers or star polymers resulting from the polymerization or copolymerization of at least one monomer containing an ethylenic group, for instance the polymers sold under the name KRATON;
polymers with a weight-average molecular mass of less than 100,000, comprising a) a polymer backbone containing hydrocarbon-based repeating units containing at least one heteroatom, and optionally b) at least one pendent fatty chain and/or at least one terminal fatty chain, which are optionally functionalized, containing from 6 to 120 carbon atoms and being linked to these hydrocarbon-based units, as described in International Patent Applications WO-A-02/056847 and WO-A-02/47619;
such as, polyamide resins (for example those comprising alkyl groups containing from 12 to 22 carbon atoms) such as those described in U.S. Pat. No. 5,783,657;
the silicone-based polyamide resins as described in European Patent Application EP-A-1266647 and in French Patent Application No. 0 216 039.

Such thickeners are, for example, described in European Patent Application EP-A-1 400 234.

For example, the at least one thickener may be an organic gelling agent, i.e. an agent comprising at least one organic compound. The organogelling agents may, for example, be chosen from those described in International Application WO-A-03/105788.

In at least one embodiment, the at least one polymeric thickener present in the composition according to the disclosure is an amorphous polymer formed by polymerization of an olefin. In another embodiment, the olefin may be an elastomeric ethylenically unsaturated monomer.

As examples of olefins, non-limiting mention may be made of ethylenic carbide monomers, such as those containing one or two ethylenic unsaturations, and containing from 2 to 5 carbon atoms, such as ethylene, propylene, butadiene or isoprene.

The at least one polymeric thickener is capable of thickening or gelling the composition. As used herein, the term "amorphous polymer" is intended to mean a polymer that does not have a crystalline form. In one embodiment, the at least one polymeric thickener may also be film-forming.

The at least one polymeric thickener may, for example, be chosen from diblock, triblock, multiblock, radial or star copolymers, and mixtures thereof.

Such polymeric thickeners are described, for example, in U.S. Patent Application Publication No. 2002/005562 and in U.S. Pat. No. 5,221,534.

In at least one embodiment, the at least one polymeric thickener is an amorphous block copolymer of styrene and of olefin.

In at least one embodiment, the at least one polymeric thickener is hydrogenated to reduce the residual ethylenic unsaturations after the polymerization of the monomers.

For example, the at least one polymeric thickener can be an optionally hydrogenated copolymer, comprising styrene blocks and ethylene/$C_3$-$C_4$ alkylene blocks.

As diblock copolymers, that may be hydrogenated, exemplary mention may be made of styrene-ethylene/propylene copolymers and styrene-ethylene/butadiene copolymers. Diblock polymers are, for example, sold under the name KRATON® G1701E by the company Kraton Polymers.

As triblock copolymers, that may be hydrogenated, exemplary mention may be made of styrene-ethylene/propylene-styrene copolymers, styrene-ethylene/butadiene-styrene copolymers, styrene-isoprene-styrene copolymers and styrene-butadiene-styrene copolymers. Triblock polymers are, for example, sold under the names KRATON® G1650, KRATON® G1652, KRATON® D1101, KRATON® D1102 and KRATON® D1160 by the company Kraton Polymers.

Use may also be made of a mixture of styrene-butylene/ethylene-styrene triblock hydrogenated copolymer and of ethylene-propylene-styrene hydrogenated star polymer, such a mixture, for example, being in isododecane. Such mixtures are, for example, sold by the company Penreco under the trade names VERSAGEL® M5960 and VERSAGEL® M5670.

In at least one embodiment, a diblock copolymer such as those described previously, such as a styrene-ethylene/propylene diblock copolymer, is used as the at least one polymeric thickener.

In at least one embodiment, the composition comprises organ clays, such as organophilic clays, which are clays modified with chemical compounds that make the clay capable of swelling.

Clays are products already known per se, which are described, for example, in the book "Minéralogie des argiles"

[Clay Mineralogy], S. Caillère, S. Hénin, M. Rautureau, 2$^{nd}$ edition 1982, Masson, the teaching of which is included herein by way of reference.

Clays are silicates containing a cation that may be chosen from calcium, magnesium, aluminium, sodium, potassium and lithium cations, and mixtures thereof.

By way of examples of clays, non-limiting mention may be made of clays of the smectite family, such as montmorillonites, hectorites, bentonites, beidellites and saponites, and also of the family of vermiculites, stevensite and chlorites.

These clays may be of natural or synthetic origin. For example, clays that are cosmetically compatible and acceptable with keratin materials are used.

For example, the organophilic clay may be chosen from montmorillonite, bentonite, hectorite, attapulgite, sepiolite, and mixtures thereof. In one embodiment, the clay is chosen from bentonites and hectorites.

These clays may be modified with at least one chemical compound chosen from quaternary amines, tertiary amines, amine acetates, imidazolines, amine soaps, fatty sulphates, alkyl aryl sulphonates, and amine oxides.

As organophilic clays, exemplary mention may be made of quaternium-18 bentonites such as those sold under the names BENTONE 3, BENTONE 38 and BENTONE 38V by the company Rheox, TIXOGEL VP by the company United Catalyst, CLAYTONE 34, CLAYTONE 40 and CLAYTONE XL by the company Southern Clay; stearalkonium bentonites such as those sold under the names BENTONE 27 by the company Rheox, TIXOGEL LG by the company United Catalyst and CLAYTONE AF and CLAYTONE APA by the company Southern Clay; quaternium-18/benzalkonium bentonites such as those sold under the names CLAYTONE HT and CLAYTONE PS by the company Southern Clay.

The fumed silicas may, for example, be obtained by high-temperature hydrolysis of a volatile silicon compound in an oxhydric flame, producing a finely divided silica. This process may make it possible to obtain hydrophilic silicas having a large number of silanol groups at their surface. Such hydrophilic silicas are, for example, marketed under the names AEROSIL 130®, AEROSIL 200®, AEROSIL 255®, AEROSIL 300® and AEROSIL 380® by the company Degussa, and CAB-O-SIL HS-5®, CAB-O-SIL EH-5®, CAB-O-SIL LM-130®, CAB-O-SIL MS-55® and CAB-O-SIL M-5® by the company Cabot.

It is possible to chemically modify the surface of said silica, via a chemical reaction generating a reduction in the number of silanol groups. It is also, for example, possible to substitute silanol groups with hydrophobic groups; a hydrophobic silica is then obtained.

Examples of hydrophobic groups include, but are not limited to:
  trimethylsiloxyl groups, which are obtained, for example, by treating fumed silica in the presence of hexamethyldisilazane. Silicas thus treated are known as "silica silylate" according to the CTFA (6$^{th}$ edition, 1995). They are, for example, marketed under the references AEROSIL R812® by the company Degussa and CAB-O-SIL TS-530® by the company Cabot;
  dimethylsilyloxyl or polydimethylsiloxane groups, which are, for example, obtained by treating fumed silica in the presence of polydimethylsiloxane or of dimethyldichlorosilane. Silicas thus treated are known as "silica dimethyl silylate" according to the CTFA (6$^{th}$ edition, 1995). They are, for example, marketed under the references AEROSIL R972® and AEROSIL R974® by the company Degussa, and CAB-O-SIL TS-610® and CAB-O-SIL TS-720® by the company Cabot.

The fumed silicas may have particle sizes ranging from nanometric to micrometric, for example ranging from 5 to 200 nm.

In one embodiment, an organomodified bentonite or hectorite is used as inorganic thickener.

The at least one thickener may be present in the composition in a total amount ranging from 0.1% to 10% by weight, relative to the total weight of the composition, such as ranging from 0.5% to 7% by weight, or for example ranging from 0.5% to 4% by weight.

Additional Compounds

The composition in accordance with the disclosure may further comprise at least one agent that is conventionally used in cosmetics, chosen, for example, from reducing agents, fatty substances, softeners, antifoams, moisturizers, UV-screening agents, inorganic colloids, peptizers, fragrances, anionic, cationic, nonionic or amphoteric surfactants, proteins, vitamins, propellants, oxyethylenated or non-oxyethylenated waxes, paraffins, $C_{10}$-$C_{30}$ fatty acids such as stearic acid and lauric acid, $C_{10}$-$C_{30}$ fatty amides such as lauric diethanolamide, and anionic, cationic, nonionic and amphoteric polymers.

The above additives are generally present in an amount for each of them ranging from 0.01% to 20% by weight, relative to the total weight of the composition.

Of course, those skilled in the art will take care to select this or these optional additive(s) in such a way that the beneficial properties intrinsically associated with the formation of the coating in accordance with the disclosure are not, or are not substantially, impaired.

The composition according to the disclosure may, for example, be in the form of a suspension, a dispersion, a solution, a gel, an emulsion, such as an oil-in-water (O/W) or water-in-oil (W/O) emulsion or a multiple emulsion (W/O/W or polyol/O/W or O/W/O), in the form of a cream, a mousse, a stick, a dispersion of vesicles, such as of ionic or nonionic lipids, a two-phase or multi-phase lotion, a spray, a powder or a paste. The composition may also, for example, be in the form of a lacquer.

Those skilled in the art may select the appropriate galenical form, and also the method for the preparation thereof, on the basis of their general knowledge, taking into account firstly the nature of the constituents used, such as their solubility in the carrier, and secondly the intended use of the composition.

The composition may, for example, be an anhydrous composition, i.e. a composition containing less than 2% by weight of water, or for example less than 0.5% of water, or for example free of water, the water not being added during the preparation of the composition, but corresponding to the residual water introduced by the mixed ingredients.

According to at least one embodiment, the composition of the disclosure is anhydrous.

The composition described above may be used on dry or wet hair and also on all types of fair or dark, natural or dyed, permanent-waved, bleached and/or relaxed hair.

According to at least one embodiment of the process of the disclosure, the hair is washed before application of the composition described above. In one embodiment, the composition is applied to clean hair.

The application may be carried out on dry or wet hair.

The application to the hair may be performed, for example, using a comb, a fine brush, a coarse brush or the fingers.

According to one embodiment, the application of the composition is subsequently followed by drying at a temperature above 40° C. In at least one embodiment, this temperature is above 45° C. In another embodiment, this temperature ranges from 45° C. to 220° C.

The drying can be carried out immediately after the application or after a leave-in time that can range from 1 minute to 30 minutes.

For example, in addition to supplying heat, the hair is dried using a flow of air. This flow of air during drying may make it possible to improve the individualization of the coating.

During drying, a mechanical action on the locks may be exerted, such as combing, brushing or running the fingers through.

The drying step of the process of the disclosure may be performed, for example, with a hood, a hairdryer, a smoothing iron, a Climazon, etc, When the drying step is performed with a hood or a hairdryer, the drying temperature may range, for example, from 40 to 110° C., for example from 50 to 90° C.

When the drying step is performed with a smoothing iron, the drying temperature may range, for example, from 110 to 220° C., for example from 140 to 200° C.

Once the drying is complete, a final rinse or shampoo wash may optionally be performed.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

By way of non-limiting illustration, concrete examples of certain embodiments of the present disclosure are given below.

EXAMPLES

Example 1

The following compositions were prepared:

| Composition | 1a | 1b | 1c | 1d | 1e |
|---|---|---|---|---|---|
| Supramolecular polymer 1a obtained using GI3000 as compound A and a graft of formula B wherein L denoted a hexamethylene radical | 8 g | — | — | — | — |
| Supramolecular polymer 1b obtained using GI3000 as compound A and a graft of formula B wherein L denoted an isophorone radical | — | 8 g | — | — | — |
| Supramolecular polymer 1c obtained using GI3000 as compound A and a graft of formula B wherein L denoted a 4,4'-dicyclohexylmethane radical | — | — | 8 g | — | — |
| Supramolecular polymer 1d obtained using GI2000 as compound A and a graft of formula B wherein L denoted a 4,4'-dicyclohexylmethane radical | — | — | — | 8 g | — |
| Supramolecular polymer 1e obtained using GI2000 as compound A and a graft of formula B wherein L denoted an isophorone radical | — | — | — | — | 8 g |
| alpha,omega-dihydroxylated polydimethylsiloxane/cyclopentadimethylsiloxane mixture (14.7/85.3) marketed by Dow Corning under the name DC1501 FLUID (*) | 14 g | 14 g | 14 g | 14 g | 14 g |
| Polymethylsilsesquioxane marketed under the name WACKER BELSIL PMS MK POWDER by the company Wacker | 3 g | 3 g | 3 g | 3 g | 3 g |

| Composition | 1a | 1b | 1c | 1d | 1e |
|---|---|---|---|---|---|
| Mica pearlescent agent coated with brown iron oxide, marketed by Eckart under the name PRESTIGE BRONZE | 6 g | 6 g | 6 g | 6 g | 6 g |
| Disteardimonium hectorite (10%) and propylene carbonate (3%) in isododecane, marketed by Elementis under the name BENTONE GEL ISD V | 8 g | 8 g | 8 g | 8 g | 8 g |
| Isododecane | qs 100 g | qs 100 g | qs 100 g | qs 100 g | qs 100 g |

(*) the concentrations indicated correspond to the pure polymer.

0.6 g of composition 1a, 1b, 1c, 1d or 1e was applied to a lock of 1 g of clean, dry hair with a tone depth of 4. Tone levels are commonly used in hair coloring. They are described, for example, in *"Science des Traitements Capillaires"* by C. Zviak, Masson 1988, p. 278. This classification is as follows:
1) Black
2) Very dark brown
3) Dark brown
4) Brown
5) Light brown
6) Dark blond
7) Blond
8) Light blond
9) Very light blond
10) Light light blond After a leave-in time of 2 minutes, the lock was dried with a hairdryer at a temperature of 80° C. for 2 minutes. A colored lock wherein the hairs were individualized and the color of which was very even and shampoo-fast was obtained.

Example 2

The following composition was prepared:

| Composition | 2 |
|---|---|
| Supramolecular polymer 1a obtained using GI3000 as compound A and a graft of formula B wherein L denoted a hexamethylene radical | 4 g |
| alpha,omega-dihydroxylated polydimethylsiloxane/cyclopentadimethylsiloxane mixture (14.7/85.3) marketed by Dow Corning under the name DC1501 FLUID (*) | 14 g |
| Mica pearlescent agent coated with brown iron oxide, marketed by Eckart under the name PRESTIGE BRONZE | 2 g |
| Ethanol | 5 g |
| Isododecane | qs 100 g |

(*) the concentration indicated corresponds to the pure polymer.

0.6 g of composition 2 was applied to a lock of 1 g of clean, wet hair having a tone depth of 4. After a leave-in time of 2 minutes, the lock was dried with a hairdryer at a temperature of 80° C. for 2 minutes. A colored lock wherein the hairs were individualized and the color of which was very even and shampoo-fast was obtained.

Example 3

The following composition is prepared:

| Composition | 1a |
|---|---|
| Supramolecular polymer 1a obtained using GI3000 as compound A and a graft of formula B wherein L denoted a hexamethylene radical | 8 g |
| alpha,omega-dihydroxylated polydimethylsiloxane/cyclopentadimethylsiloxane mixture (14.7/85.3) marketed by Dow Corning under the name DC1501 FLUID (*) | 14 g |
| Polymethylsilsesquioxane marketed under the name WACKER BELSIL PMS MK POWDER by the company Wacker | 3 g |
| Mica pearlescent agent coated with brown iron oxide, marketed by Eckart under the name PRESTIGE BRONZE | 6 g |
| Disteardimonium hectorite (10%) and propylene carbonate (3%) in isododecane, marketed by Elementis under the name BENTONE GEL ISD V | 8 g |
| Isododecane | qs 100 g |

(*) the concentration indicated corresponds to the pure polymer.

0.6 g of composition 1a was applied to a lock of 1 g of clean, dry hair having a tone depth of 4. After a leave-in time of 2 minutes, the lock was dried with a smoothing iron at 130° C. for one minute. The lock was then combed. A colored lock wherein the hairs were individualized and the color of which was very even and shampoo-fast was obtained.

Example 4

The following composition was prepared:

| Composition | 3 |
|---|---|
| Supramolecular polymer 1a obtained using GI3000 as compound A and a graft of formula B wherein L denoted a hexamethylene radical | 8 g |
| alpha,omega-dihydroxylated polydimethylsiloxane/cyclopentadimethylsiloxane mixture (14.7/85.3) marketed by Dow Corning under the name DC1501 FLUID (*) | 14 g |
| Polymethylsilsesquioxane marketed under the name WACKER BELSIL PMS MK POWDER by the company Wacker | 3 g |
| Trimethylsiloxysilicate resin marketed under the name SR1000 by Momentive Performance Materials | 2 g |
| Mica pearlescent agent coated with brown iron oxide, marketed by Eckart under the name PRESTIGE BRONZE | 6 g |
| Disteardimonium hectorite (10%) and propylene carbonate (3%) in isododecane, marketed by Elementis under the name BENTONE GEL ISD V | 8 g |
| Isododecane | qs 100 g |

(*) the concentration indicated corresponds to the pure polymer.

0.6 g of composition 3 was applied to a lock of 1 g of clean, wet hair having a tone depth of 4. After a leave-in time of 2 minutes, the lock was dried with a hairdryer at a temperature of 80° C. for 2 minutes. A colored lock wherein the hairs were individualized and the color of which was very even and shampoo-fast was obtained.

The supramolecular polymers used in the examples above were synthesized in the following way.

Polymer 1a: 100 g of GI3000 polymer marketed by the company Nisso was dried at 80° C. under vacuum overnight. This polymer was dissolved in 400 ml of anhydrous toluene 25 µl of catalyst, dibutyltin dilaurate, was added to the reaction mixture. The medium was heated at 80° C. and mixed until a homogeneous solution was obtained. 15 g of isocyanate-functionalized molecule having the following structure:

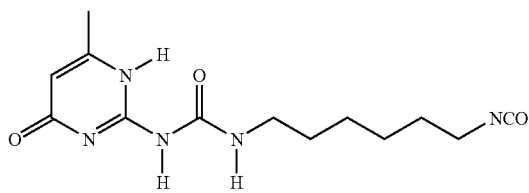

was added in solution in 300 ml of anhydrous toluene, under a controlled atmosphere at 40° C. The reaction mixture was heated to 100° C. and stirred at this temperature for 4 hours. The reaction was monitored by infrared spectroscopy, with monitoring of the total disappearance of the peak characteristic of the isocyanates at 2260 cm$^{-1}$. At the end of the reaction, 100 ml of ethanol was added in order to remove any trace of residual isocyanate. The mixture was filtered after having added isododecane in order to make the solution less viscous. The polymer solution was then directly stripped with isododecane. The final polymer was obtained at a 21% solids content in isododecane and was characterized by GC (Mn=6400 and a polydispersity index PI of 1.85) and $^1$H NMR (spectrum in accordance with what is expected).

Polymer 1b: 99 g of GI3000 polymer marketed by the company Nisso, in the presence of 22 mg of catalyst, dibutyltin dilaurate, were heated at 80° C. under vacuum for 2 hours. The temperature of the mixture was brought down to 20° C. under argon. 11 g of IPDI (isophorone diisocyanate) was added, as was 30 ml of isododecane. The mixture was stirred for 16 hours at 20° C., under a controlled atmosphere, and was then heated to 120° C., followed by the addition of 25 ml of propylene carbonate. 8.1 g of 6-methylisocytosine was added. This resulted in a homogeneous white suspension. This suspension was heated to 140° C. and stirred at this temperature for 6 hours. The reaction was monitored by infrared spectroscopy, until total disappearance of the peak characteristic of the isocyanates (2250 cm$^{-1}$). The mixture was then brought back down to 30° C., and 1 liter of heptane was added to the mixture, before filtration through celite. Stripping with isododecane made it possible to obtain the polymer 1b at a 20% solids content. The polymer was characterized by GC (Mn=4200 with a PI of 2.34).

Polymer 1c: 89 g of GI3000 polymer marketed by the company Nisso, in the presence of 22 mg of catalyst, dibutyltin dilaurate, was heated at 80° C. under vacuum for 2 hours. The temperature of the mixture was brought down to 20° C. under argon. 11.6 g of 4,4'-dicyclohexylmethane diisocyanate was added, followed by the addition of 60 ml of isododecane. The mixture was stirred for 16 hours at 20° C., under a controlled atmosphere, and was then heated to 120° C., followed by the addition of 40 ml of propylene carbonate. 6.64 g of 6-methylisocytosine were added. This resulted in a homogeneous white suspension. This suspension was heated to 140° C. and stirred at this temperature for 8 hours. The reaction was monitored by infrared spectroscopy, until total disappearance of the peak characteristic of the isocyanates (2250 cm$^{-1}$). The mixture was then brought back down to 30° C., and 250 ml of isododecane and also 500 ml of heptane were added to the mixture, before filtration through celite. Stripping with isododecane made it possible to obtain the polymer 1c at a 22% solids content. The polymer was characterized by GC (Mn=10 700 with a PI of 2.26).

Polymer 1d: 143.1 g of G12000 polymer marketed by the company Nisso, in the presence of 33 mg of catalyst, dibutyltin dilaurate, was heated at 80° C. under vacuum for 2 hours. The temperature of the mixture was brought down to 20° C. under argon, followed by the addition of 85 ml of isododecane. 30.8 g of 4,4'-dicyclohexylmethane diisocyanate was added. The mixture was stirred for 16 hours at 20° C., under a controlled atmosphere, and was then heated to 120° C., followed by the addition of 70 ml of propylene carbonate. 22.6 g of 6-methylisocytosine was added. This resulted in a homogeneous white suspension. This suspension was heated to 140° C. and was stirred at this temperature for 8 hours. The reaction was monitored by infrared spectroscopy, until total disappearance of the peak characteristic of the isocyanates (2250 cm$^{-1}$). The mixture was then brought back down to 20° C., and 700 ml of isododecane and also 500 ml of heptane were added to the mixture, before filtration through celite. Stripping with isododecane made it possible to obtain the polymer 1d at a 20% solids content. The polymer was characterized by GC (Mn=8400 with a PI of 2.00).

Polymer 1e: 106.1 g of G12000 polymer marketed by the company Nisso, in the presence of 22 mg of catalyst, dibutyltin dilaurate, were heated at 80° C. under vacuum for 2 hours. The temperature of the mixture was brought down to 20° C. under argon, followed by the addition of 10 ml of isododecane. 19.3 g of isophorone diisocyanate were added. The mixture was stirred for 16 hours at 20° C., under a controlled atmosphere, and was then heated to 120° C., followed by the addition of 25 ml of propylene carbonate. 12 g of 6-methylisocytosine were added. This resulted in a homogenous white suspension. This suspension was heated to 140° C. and was stirred at this temperature for 6 hours. The reaction was monitored by infrared spectroscopy, until total disappearance of the peak characteristic of the isocyanates (2250 cm$^{-1}$). The mixture was then brought back down to 30° C., and 400 ml of heptane, 200 ml of THF and 50 ml of ethanol were added to the mixture, before filtration through celite. Stripping with isododecane made it possible to obtain the polymer 1e at a 20% solids content. The polymer was characterized by GC (Mn=7000 with a PI of 2.05).

What is claimed is:

1. A composition for dyeing keratin fibers, comprising at least one polyalkene-based supramolecular polymer, at least one pigment and at least one volatile solvent, wherein the weight ratio of the at least one polyalkene-based supramolecular polymer to the at least one pigment has a value of greater than 0.25; and wherein at least one polyalkene of the at least one polyalkene-based supramolecular polymer is chosen from poly(ethylene-butylene)s, polybutadienes and polyisoprenes.

2. The composition according to claim 1, wherein the at least one polyalkene-based supramolecular polymer is derived from the condensation of at least one polyalkene polymer functionalized with at least one reactive group (a), with at least one graft functionalized with at least one reactive group (b), wherein the at least one reactive group (b) is capable of reacting with the at least one reactive group (a), and wherein the at least one graft comprises at least one group capable of forming at least three H-bonds.

3. The composition according to claim 2, wherein the at least one functionalized polyalkene is chosen from those of formula HX—R—X'H, wherein
XH and X'H are reactive groups, with X and X', which are identical or different, chosen from O, S, NH or $NR_a$, $R_a$ representing a $C_1$-$C_6$ alkyl group; and
R is chosen from poly(ethylene-butylene)s, polybutadienes and polyisoprenes.

4. The composition according to claim 1, wherein the at least one functionalized polyalkene is chosen from hydroxyl-terminated poly(ethylene-butylene)s, hydroxyl-terminated polybutadienes and hydroxyl-terminated polyisoprenes.

5. The composition according to claim 2, wherein the at least one graft has at least one ureidopyrimidone group.

6. The composition according to claim 2, wherein the at least one reactive group of the at least one graft is chosen from isocyanate groups.

7. The composition according to claim 2, wherein the at least one graft is chosen from entities of formula (B):

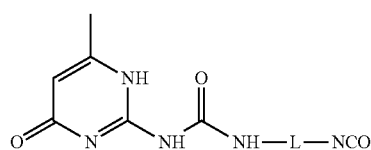

(B)

wherein L is chosen from phenylene; 1,4-nitrophenyl; 1,2-ethylene; 1,6-hexylene; 1,4-butylene; 1,6-(2,4,4-trimethylhexylene); 1,4-(4-methylpentylene); 1,5-(5-methylhexylene); 1,6-(6-methylheptylene); 1,5-(2,2,5-trimethylhexylene); 1,7-(3,7-dimethyloctylene); -isophorone-; 4,4'-methylenebiscyclohexylene; tolylene; 2-methyl-1,3-phenylene; 4-methyl-1,3-phenylene; and 4,4-biphenylenemethylene groups.

8. The composition according to claim 1, wherein the at least one polyalkene-based supramolecular polymer is obtained by condensing at least one polymer (A1) comprising a polyalkene part chosen from poly(ethylene-butylene)s, polybutadienes and polyisoprenes, the at least one polymer (A1) being functionalized with at least one reactive group (B1), with at least one molecule (A3) comprising at least one reactive group (B2), the at least one molecule (A3) being such that, after reaction of the at least one (B1) and the at least one (B2) groups, an entity capable of forming at least three H-bonds is formed.

9. The composition according to claim 8, wherein the at least one polymer (A1) is chosen from those of formula (C1):

(C1)

wherein X and X', which may be identical or different, are chosen from O, S, NH and $NR_a$, $R_a$ representing a $C_1$-$C_6$ alkyl group;
R is chosen from poly(ethylene-butylene)s, polybutadienes and polyisoprenes; and
L is chosen from phenylene; 1,4-nitrophenyl; 1,2-ethylene; 1,6-hexylene; 1,4-butylene; 1,6-(2,4,4-trimethylhexylene); 1,4-(4-methylpentylene); 1,5-(5-methylhexylene); 1,6-(6-methylheptylene); 1,5-(2,2,5-trimethylhexylene); 1,7-(3,7-dimethyloctylene); -isophorone-; 4,4'-methylenebiscyclohexylene; tolylene; 2-methyl-1,3-phenylene; 4-methyl-1,3-phenylene; and 4,4-biphenylenemethylene.

10. The composition according to claim 8, wherein the at least one molecule (A3) is 6-methylisocytosine of formula:

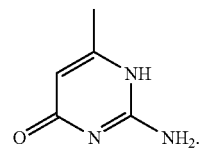

11. The composition according to claim 1, wherein the at least one polyalkene-based supramolecular polymer is chosen from those of formula (C):

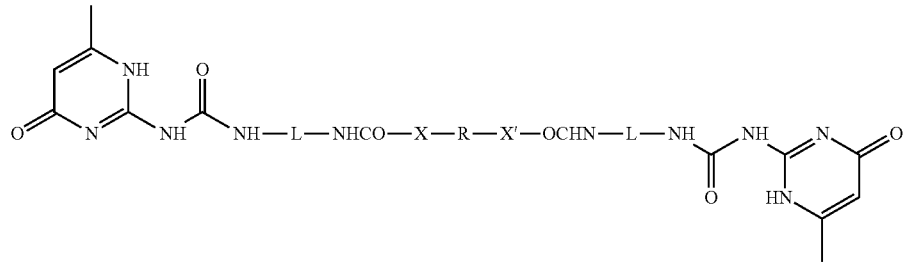

(C)

wherein X and X', which may be identical or different, are chosen from O, S, NH and $NR_a$, $R_a$ representing a $C_1$-$C_6$ alkyl group;
R is chosen from poly(ethylene-butylene)s, polybutadienes and polyisoprenes; and
and L is chosen from phenylene; 1,4-nitrophenyl; 1,2-ethylene; 1,6-hexylene; 1,4-butylene; 1,6-(2,4,4-trimethylhexylene); 1,4-(4-methylpentylene); 1,5-(5-methylhexylene); 1,6-(6-methylheptylene); 1,5-(2,2,5-trimethylhexylene); 1,7-(3,7-dimethyloctylene); -isophorone-; 4,4'-methylenebiscyclohexylene; tolylene; 2-methyl-1,3-phenylene; 4-methyl-1,3-phenylene; and 4,4-biphenylenemethylene.

12. The composition according to claim 1, wherein the at least one volatile solvent is chosen from water and non-silicone and silicone organic solvents.

13. The composition according to claim 1, further comprising at least one silicone compound chosen from polysiloxanes having a viscosity of greater than 100 cst and grafted silicone compounds.

14. A process for dyeing keratin fibers, comprising applying to the keratin fibers, a composition comprising at least one polyalkene-based supramolecular polymer, at least one pigment and at least one volatile solvent, wherein the weight ratio of the at least one polyalkene-based supramolecular polymer to the at least one pigment has a value greater than 0.25; and wherein at least one polyalkene of the at least one polyalkene-based supramolecular polymer is chosen from poly(ethylene-butylene)s, polybutadienes and polyisoprenes; and optionally drying the keratin fibers at a temperature above 40° C.

15. The composition according to claim 8, wherein the at least one molecule (A3) is such that, after reaction of the at least one (B1) and at least one (B2) groups, an entity capable of forming at least four H-bonds is formed.

* * * * *